United States Patent
Lee et al.

(10) Patent No.: US 10,557,140 B2
(45) Date of Patent: Feb. 11, 2020

(54) CTLA-4-TARGETING TRANS-SPLICING RIBOZYME FOR DELIVERY OF CHIMERIC ANTIGEN RECEPTOR, AND USE THEREOF

(71) Applicant: INDUSTRY-ACADEMIC COOPERATION FOUNDATION, DANKOOK UNIVERSITY, Gyeonggi-do (KR)

(72) Inventors: Seong Wook Lee, Seoul (KR); Bit Na Yang, Gyeongsangbuk-do (KR); Sung Jin Kim, Seoul (KR); Seung Ryul Han, Seoul (KR)

(73) Assignee: INDUSTRY-ACADEMIC COOPERATION FOUNDATION, DANKOOK UNIVERSITY, Gyeonggi-do (KR)

( * ) Notice: Subject to any disclaimer, the term of this patent is extended or adjusted under 35 U.S.C. 154(b) by 0 days.

(21) Appl. No.: 15/548,362

(22) PCT Filed: Feb. 2, 2016

(86) PCT No.: PCT/KR2016/001106
§ 371 (c)(1),
(2) Date: Aug. 2, 2017

(87) PCT Pub. No.: WO2016/126071
PCT Pub. Date: Aug. 11, 2016

(65) Prior Publication Data
US 2019/0225969 A1  Jul. 25, 2019

(30) Foreign Application Priority Data
Feb. 2, 2015 (KR) .................. 10-2015-0016152

(51) Int. Cl.
| | | |
|---|---|---|
| *C12N 15/113* | (2010.01) | |
| *A61K 35/17* | (2015.01) | |
| *C12N 7/00* | (2006.01) | |
| *C12N 9/14* | (2006.01) | |
| *C12N 15/62* | (2006.01) | |

(Continued)

(52) U.S. Cl.
CPC .......... *C12N 15/1138* (2013.01); *A61K 35/17* (2013.01); *A61K 35/76* (2013.01); *A61K 39/0011* (2013.01); *A61P 35/00* (2018.01); *C07K 19/00* (2013.01); *C12N 7/00* (2013.01); *C12N 9/14* (2013.01); *C12N 15/62* (2013.01); *C12N 15/63* (2013.01); *C12N 15/86* (2013.01); *A61K 2039/5156* (2013.01); *C12N 2310/11* (2013.01); *C12N 2310/12* (2013.01); *C12N 2310/124* (2013.01); *C12N 2310/3519* (2013.01); *C12N 2320/11* (2013.01); *C12N 2330/31* (2013.01); *C12N 2330/51* (2013.01)

(58) Field of Classification Search
None
See application file for complete search history.

(56) References Cited

U.S. PATENT DOCUMENTS

| | | |
|---|---|---|
| 8,822,647 B2 | 9/2014 | Jensen |
| 2014/0286905 A1* | 9/2014 | Lee ................. A61K 35/761 424/93.2 |

FOREIGN PATENT DOCUMENTS

| | | |
|---|---|---|
| KR | 10-2010-0024055 A | 3/2010 |
| KR | 10-2012-0132594 A | 12/2012 |
| KR | 10-2013-0020492 A | 2/2013 |

OTHER PUBLICATIONS

International Application No. PCT/KR2016/001106, International Search Report and Written Opinion, dated May 31, 2016.
(Continued)

*Primary Examiner* — Tracy Vivlemore
(74) *Attorney, Agent, or Firm* — Marshall, Gerstein & Borun LLP

(57) ABSTRACT

The present invention relates to a recombinant vector, characterized by including a cytotoxic T-lymphocyte-associated protein-4 (CTLA-4)-targeting trans-splicing ribozyme expression cassette for delivery of chimeric antigen receptor, wherein the expression cassette includes: (i) a CTLA-4-targeting trans-splicing ribozyme; and (ii) a polynucleotide encoding a chimeric antigen receptor ligated to the 3' exon of the ribozyme. The present invention also relates to a transformed cell into which the recombinant vector is introduced, a ribozyme expressed from the recombinant vector, a retrovirus expressing the ribozyme, and a T cell treated with the retrovirus. Furthermore, the present invention relates to a pharmaceutical composition for preventing or treating cancers, in which the pharmaceutical composition includes the recombinant vector, the transformed cell, the ribozyme, the retrovirus, the T cell, or a combination thereof; and a method for treating cancers, in which the method includes administering, to an individual in need thereof, the recombinant vector, the transformed cell, the ribozyme, the retrovirus, the T cell, or a combination thereof. The recombinant vector of the present invention and the ribozyme expressed therefrom become a gene-cell therapy which inhibits CTLA-4 on T cells which has been an obstacle in conventional anti-cancer therapies and, at the same time, enables anti-cancer treatment, thereby allowing more effective anti-cancer effects to be anticipated. Such a gene-cell therapy results in decreased toxicity in normal tissues and thus exhibits increased effects in both therapeutic efficacy and safety, which enables it to be widely utilized in the field of gene therapy in the future.

13 Claims, 15 Drawing Sheets
Specification includes a Sequence Listing.

(51) Int. Cl.
    *C12N 15/63*    (2006.01)
    *C12N 15/86*    (2006.01)
    *A61K 35/76*    (2015.01)
    *C07K 19/00*    (2006.01)
    *A61P 35/00*    (2006.01)
    *A61K 39/00*    (2006.01)

(56) References Cited

OTHER PUBLICATIONS

John et al., Anti-PD-1 antibody therapy potently enhances the eradication of established tumors by gene-modified T cells, Clin. Cancer Res., 19(20):5636-46 (2013).
Kwon et al., Specific regression of human cancer cells by ribozyme-mediated targeted replacement of tumor-specific transcript, Mol. Ther., 12(5):824-34 (2005).

* cited by examiner

After transfection with retrovirus (centrifugation for 1 hour and a half, followed by incubation for 2 hours), at the time of medium replacement, the medium was replaced with a medium with and without chemical, and experiments conducted 72 hours later

SEQUENCE LISTING

```
<160> NUMBER OF SEQ ID NOS: 38

<210> SEQ ID NO 1
<211> LENGTH: 407
<212> TYPE: DNA
<213> ORGANISM: Artificial Sequence
<220> FEATURE:
<223> OTHER INFORMATION: CTLA-4(IGS48) targeting ribozyme

<400> SEQUENCE: 1
atcctatgga tagaaaagtt atcaggcatg cacctggtag ctagtcttta aaccaataga      60
ttgcatcggt ttaaaaggca agaccgtcaa attgcgggaa agggtcaac agccgttcag     120 taccaagtct caggggaaac tttgagatgg ccttgcaaag ggtatggtaa taagctgacg     180
gacatggtcc taaccacgca gccaagtcct aagtcaacag atcttctgtt gatatggatg     240
cagttcacag actaaatgtc ggtcgggaa gatgtattct tctcataaga tatagtcgga     300
cctctcctta atgggagcta gcggatgaag tgatgcaaca ctggagccgc tgggaactaa     360
tttgtatgcg aaagtatatt gattagtttt ggagtactcg ttaggat                  407

<210> SEQ ID NO 2
<211> LENGTH: 403
<212> TYPE: DNA
<213> ORGANISM: Artificial Sequence
<220> FEATURE:
<223> OTHER INFORMATION: CTLA-4(IGS111) targeting ribozyme

<400> SEQUENCE: 2
tttgccttta aaagttatca ggcatgcacc tggtagctag tctttaaacc aatagattgc      60
atcggtttaa aaggcaagac cgtcaaattg cgggaaaggg gtcaacagcc gttcagtacc     120
aagtctcagg ggaaactttg agatggcctt gcaagggta tggtaataag ctgacggaca     180
tggtcctaac cacgcagcca agtcctaagt caacagatct tctgttgata tggatgcagt     240
tcacagacta aatgtcggtc ggggaagatg tattcttctc ataagatata gtcggacctc     300
tccttaatgg gagctagcgg atgaagtgat gcaacactgg agccgctggg aactaatttg     360
tatgcgaaag tatattgatt agttttggag tactcgtaag gat                      403

<210> SEQ ID NO 3
```

```
<211> LENGTH: 411
<212> TYPE: DNA
<213> ORGANISM: Artificial Sequence
<220> FEATURE:
<223> OTHER INFORMATION: CTLA-4(IGS232) targeting ribozyme

<400> SEQUENCE: 3
agcttatcct ttgacaggaa aagttatcag gcatgcacct ggtagctagt ctttaaacca    60
atagattgca tcggtttaaa aggcaagacc gtcaaattgc gggaaagggg tcaacagccg   120
ttcagtacca agtctcaggg gaaactttga gatggccttg caaagggtat ggtaataagc   180
tgacggacat ggtcctaacc acgcagccaa gtcctaagtc aacagatctt ctgttgatat   240
ggatgcagtt cacagactaa atgtcggtcg gggaagatgt attcttctca taagatatag   300
tcggacctct ccttaatggg agctagcgga tgaagtgatg caacactgga gccgctggga   360
actaatttgt atgcgaaagt atattgatta gttttggagt actgtaagga t            411

<210> SEQ ID NO 4
<211> LENGTH: 2364
<212> TYPE: DNA
<213> ORGANISM: Artificial Sequence
<220> FEATURE:
<223> OTHER INFORMATION: Tag72-CAR

<400> SEQUENCE: 4
atggaatgga gctgggtctt tctcttcttc ctgtcagtaa ctacaggtgt ccactcccag    60
gtccagcttg tgcagtctgg ggctgaagtg aagaagcctg ggcttcagt gaaggtgtcc    120 tgcaaggctt ctggctacac cttcactgac atgcaattc actgggtgcg ccaggcccct    180
ggacaacgcc ttgagtggat gggatatttt tctcctggca cgatgatttt aaatactcc    240 cagaagttcc agggacgcgt gacaatcact gcggacaaat ccgcgagcac agcctacatg    300
gagctgagca gcctgagatc tgaggacacg gcggtctatt actgtgcaag atcgtggatc    360
atgcagtact ggggccaagg gactctggtc actgtctctt caggtggagg cggttcaggc    420
ggaggtggct ctggcggtgg cggatcggac attgtgatga cccagtctcc agactccctg    480
gctgtgtctc tgggcgagag ggccaccatc aactgcaagt ccagccagag tgttttatac    540
agcagcaaca ataagaacta cttagcttgg taccagcaga aaccaggaca gcctcctaag    600
ctgctcattt actgggcatc tacccgggaa tccggggtcc ctgaccgatt cagtggcagc    660
gggtctggga cagatttcac tctcaccatc agcagcctgc aggctgaaga tgtggcagtt    720
tattactgtc agcaatatta ttcctatccg ttgacgttcg gccaagggac caaggtggaa    780
atcaaacgct ggccaggttc tccaaaggca caggcctcct ccgtgcccac tgcacaaccc    840
caagcagagg gcagcctcgc caaggcaacc acagccccag ccaccaccg taacacaggt    900 agaggaggag aagagaagaa gaaggagaag gagaaagagg aacaagaaga gagagagaca    960
aagcacccag gttgtccgga gcccaaatct tgtgacaaaa ctcacacatg cccaccgtgc   1020
ccagcacctg aactcctggg gggaccgtca gtcttcctct tcccccccaaa acccaaggac   1080 accctcatga tctcccggac ccctgaggtc acatgcgtgg tggtggacgt gagccacgaa   1140
gaccctgagg tcaagttcaa ctggtacgtg gacggcgtgg aggtgcataa tgccaagaca   1200
aagccgcggg aggagcagta caacagcacg taccgggtgg tcagcgtcct caccgtcctg   1260
caccaggact ggctgaatgg caaggagtac aagtgcaagg tctccaacaa agccctccca   1320
gcccccatcg agaaaaccat ctccaaagcc aagggcagc cccgagaacc acaggtgtac   1380
accctgcccc catcccggga tgagctgacc aagaaccagg tcagcctgac ctgcctggtc   1440
```

```
aaaggcttct atcccagcga catcgccgtg gagtgggaga gcaatgggca gccggagaac      1500
aactacaaga ccacgcctcc cgtgctggac tccgacggct ccttcttcct ctacagcaag      1560
ctcaccgtgg acaagagcag gtggcagcag gggaacgtct tctcatgctc cgtgatgcat      1620
gaggctctgc acaaccacta cacgcagaag agcctctccc tgtctccggg taaattttgg      1680
gtgctggtgg tggttggtgg agtcctggct tgctatagct tgctagtaac agtggccttt      1740
attattttct gggtgaggag taagaggagc aggctcctgc acagtgacta catgaacatg      1800
actccccgcc gccccgggcc cacccgcaag cattaccagc cctatgcccc accacgcgac      1860
ttcgcagcct atcgctccgc cctgtacctg ctccggaggg accagaggct gcccccccgat      1920 gcccacaagc ccctgggggg aggcagtttc cggaccccca tccaagagga gcaggccgac      1980
gcccactcca ccctggccaa gatcagagtg aaattcagca ggagcgcaga cgcccccgcg      2040
taccagcagg gccagaacca gctctataac gagctcaatc taggacgaag agaggagtac      2100
gatgttttgg acaagagacg tggccgggac cctgagatgg ggggaaagcc gcagagaagg      2160
aagaaccctc aggaaggcct gtacaatgaa ctgcagaaag ataagatggc ggaggcctac      2220
agtgagattg ggatgaaagg cgagcgccgg aggggcaagg ggcacgatgg cctttaccag      2280
ggtctcagta cagccaccaa ggacacctac gacgcccttc acatgcaggc cctgccccct      2340
cgccatcatc accatcacca ttaa                                            2364

<210> SEQ ID NO 5
<211> LENGTH: 101
<212> TYPE: DNA
<213> ORGANISM: Artificial Sequence
<220> FEATURE:
<223> OTHER INFORMATION: CTLA4 specific antisense 100

<400> SEQUENCE: 5
agccatggct ttatgggagc ggtgttcagg tcttcaggaa gtagagcaaa acctttcagg       60
atcctgaagc tttgaaatgt gtttgaaccc acacagaatc a                         101

<210> SEQ ID NO 6
<211> LENGTH: 301
<212> TYPE: DNA
<213> ORGANISM: Artificial Sequence
<220> FEATURE:
<223> OTHER INFORMATION: CTLA4 specific antisense 300

<400> SEQUENCE: 6
acctcagtgg ctttgcctgg agatgcatac tcacacacaa agctggcgat gcctcggctg       60
ctggccagta ccacagcagg ctgggccacg tgcattgctt tgcagaagac agggatgaag      120
agaagaaaaa acaggagagt gcagggccag gtcctggtag ccaggttcag ctgagccttg      180
tgccgctgaa atccaaggca agccatggct ttatgggagc ggtgttcagg tcttcaggaa      240
gtagagcaaa acctttcagg atcctgaagc tttgaaatgt gtttgaaccc acacagaatc      300
a                                                                     301

<210> SEQ ID NO 7
<211> LENGTH: 588
<212> TYPE: DNA
<213> ORGANISM: Artificial Sequence
<220> FEATURE:
<223> OTHER INFORMATION: CMV promoter

<400> SEQUENCE: 7
```

| | |
|---|---:|
| gttgacattg attattgact agttattaat agtaatcaat tacgggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctc | 588 |

<210> SEQ ID NO 8
<211> LENGTH: 2777
<212> TYPE: DNA
<213> ORGANISM: Artificial Sequence
<220> FEATURE:
<223> OTHER INFORMATION: CTLA4 Rib48-CAR sequence

<400> SEQUENCE: 8

| | |
|---|---:|
| atcctatgga tagaaaagtt atcaggcatg cacctggtag ctagtcttta aaccaataga | 60 |
| ttgcatcggt ttaaaggca agaccgtcaa attgcgggaa aggggtcaac agccgttcag | 120 |
| taccaagtct caggggaaac tttgagatgg ccttgcaaag ggtatggtaa taagctgacg | 180 |
| gacatggtcc taaccacgca gccaagtcct aagtcaacag atcttctgtt gatatggatg | 240 |
| cagttcacag actaaatgtc ggtcgggaa gatgtattct tctcataaga tatagtcgga | 300 |
| cctctcctta tgggagcta gcggatgaag tgatgcaaca ctggagccgc tgggaactaa | 360 |
| tttgtatgcg aaagtatatt gattagtttt ggagtactcg ttaggatgga tccatggaat | 420 |
| ggagctgggt ctttctcttc ttcctgtcag taactacagg tgtccactcc caggtccagc | 480 |
| ttgtgcagtc tggggctgaa gtgaagaagc ctggggcttc agtgaaggtg tcctgcaagg | 540 |
| cttctggcta caccttcact gaccatgcaa ttcactgggt gcgccaggcc cctggacaac | 600 |
| gccttgagtg gatgggatat ttttctcctg gcaacgatga ttttaaatac tcccagaagt | 660 |
| tccagggacg cgtgacaatc actgcggaca atccgcgag cacagcctac atggagctga | 720 |
| gcagcctgag atctgaggac acggcggtct attactgtgc aagatcgtgg atcatgcagt | 780 |
| actggggcca agggactctg gtcactgtct cttcaggtgg aggcggttca ggcggaggtg | 840 |
| gctctggcgg tggcggatcg acattgtga tgacccagtc tccagactcc ctggctgtgt | 900 |
| ctctgggcga gagggccacc atcaactgca agtccagcca gagtgtttta tacagcagca | 960 |
| acaataagaa ctacttagct tggtaccagc agaaaccagg acagcctcct aagctgctca | 1020 |
| tttactgggc atctacccgg gaatccgggg tccctgaccg attcagtggc agcgggtctg | 1080 |
| ggacagattt cactctcacc atcagcagcc tgcaggctga gatgtggca gtttattact | 1140 |
| gtcagcaata ttattcctat ccgttgacgt tcggccaagg accaaggtg gaaatcaaac | 1200 |
| gctggccagt ttccaaaag gcacaggcct cctccgtgcc cactgcacaa ccccaagcag | 1260 |
| agggcagcct cgccaaggca accacagccc agccaccac ccgtaacaca ggtagaggag | 1320 |
| gagaagagaa gaaggaggag aaggagaaag aggaacaaga agagagagag acaaagacac | 1380 |
| caggttgtcc ggagcccaaa tcttgtgaca aaactcacac atgcccaccg tgcccagcac | 1440 |
| ctgaactcct ggggggaccg tcagtcttcc tcttcccccc aaaacccaag gacaccctca | 1500 |

```
tgatctcccg gacccctgag gtcacatgcg tggtggtgga cgtgagccac gaagaccctg   1560
aggtcaagtt caactggtac gtggacggcg tggaggtgca taatgccaag acaaagccgc   1620
gggaggagca gtacaacagc acgtaccggg tggtcagcgt cctcaccgtc ctgcaccagg   1680
actggctgaa tggcaaggag tacaagtgca aggtctccaa caaagccctc ccagccccca   1740
tcgagaaaac catctccaaa gccaaagggc agccccgaga accacaggtg tacaccctgc   1800
ccccatcccg ggatgagctg accaagaacc aggtcagcct gacctgcctg gtcaaaggct   1860
tctatcccag cgacatcgcc gtggagtggg agagcaatgg gcagccggag aacaactaca   1920
agaccacgcc tcccgtgctg gactccgacg gctccttctt cctctacagc aagctcaccg   1980
tggacaagag caggtggcag caggggaacg tcttctcatg ctccgtgatg catgaggctc   2040
tgcacaacca ctacacgcag aagagcctct ccctgtctcc gggtaaattt tgggtgctgg   2100
tggtggttgg tggagtcctg gcttgctata gcttgctagt aacagtggcc tttattattt   2160
tctgggtgag gagtaagagg agcaggctcc tgcacagtga ctacatgaac atgactcccc   2220
gccgccccgg gcccacccgc aagcattacc agccctatgc cccaccacgc gacttcgcag   2280
cctatcgctc cgccctgtac ctgctccgga gggaccagag gctgccccc gatgcccaca   2340 agcccctggg ggaggcagt ttccggaccc ccatccaaga ggagcaggcc gacgcccact   2400
ccaccctggc caagatcaga gtgaaattca gcaggagcgc agacgccccc gcgtaccagc   2460
agggccagaa ccagctctat aacgagctca atctaggacg aagagaggag tacgatgttt   2520
tggacaagag acgtggccgg gaccctgaga tggggggaaa gccgcagaga aggaagaacc   2580
ctcaggaagg cctgtacaat gaactgcaga agataagat ggcggaggcc tacagtgaga   2640
ttgggatgaa aggcgagcgc cggagggca aggggcacga tggcctttac cagggtctca   2700
gtacagccac caaggacacc tacgacgccc ttcacatgca ggccctgccc cctcgccatc   2760
atcaccatca ccattaa                                                  2777
```

<210> SEQ ID NO 9
<211> LENGTH: 2884
<212> TYPE: DNA
<213> ORGANISM: Artificial Sequence
<220> FEATURE:
<223> OTHER INFORMATION: AS100-CTLA4 Rib48-CAR sequence

<400> SEQUENCE: 9

```
agccatggct ttatgggagc ggtgttcagg tcttcaggaa gtagagcaaa acctttcagg     60
atcctgaagc tttgaaatgt gtttgaaccc acacagaatc aaagcttatc ctatggatag    120
aaaagttatc aggcatgcac ctggtagcta gtctttaaac caatagattg catcggttta    180
aaaggcaaga ccgtcaaatt gcgggaaagg ggtcaacagc cgttcagtac caagtctcag    240
ggaaactttt gagatggcct tgcaaagggt atggtaataa gctgacggac atggtcctaa    300
ccacgcagcc aagtcctaag tcaacagatc ttctgttgat atggatgcag ttcacagact    360
aaatgtcggt cggggaagat gtattcttct cataagatat agtcggacct ctccttaatg    420
ggagctagcg gatgaagtga tgcaacactg gagccgctgg gaactaattt gtatgcgaaa    480
gtatattgat tagttttgga gtactcgtta ggatggatcc atggaatgga gctgggtctt    540
tctcttcttc ctgtcagtaa ctacaggtgt ccactcccag gtccagcttg tgcagtctgg    600
ggctgaagtg aagaagcctg gggcttcagt gaaggtgtcc tgcaaggctt ctggctacac    660
cttcactgac catgcaattc actgggtgcg ccaggccct ggacaacgcc ttgagtggat    720
```

```
gggatatttt tctcctggca acgatgattt taaatactcc cagaagttcc agggacgcgt      780
gacaatcact gcggacaaat ccgcgagcac agcctacatg gagctgagca gcctgagatc      840
tgaggacacg gcggtctatt actgtgcaag atcgtggatc atgcagtact ggggccaagg      900
gactctggtc actgtctctt caggtggagg cggttcaggc ggaggtggct ctggcggtgg      960
cggatcggac attgtgatga cccagtctcc agactccctg gctgtgtctc tgggcgagag     1020
ggccaccatc aactgcaagt ccagccagag tgttttatac agcagcaaca ataagaacta     1080
cttagcttgg taccagcaga aaccaggaca gcctcctaag ctgctcattt actgggcatc     1140
tacccgggaa tccggggtcc ctgaccgatt cagtggcagc gggtctggga cagatttcac     1200
tctcaccatc agcagcctgc aggctgaaga tgtggcagtt tattactgtc agcaatatta     1260
ttcctatccg ttgacgttcg gccaaggac caaggtggaa atcaaacgct ggccaggttc     1320
tccaaaggca caggcctcct ccgtgcccac tgcacaaccc caagcagagg gcagcctcgc     1380
caaggcaacc acagccccag ccaccacccg taacacaggt agaggaggag aagagaagaa     1440
gaaggagaag gagaaagagg aacaagaaga gagagagaca aagacaccag gttgtccgga     1500
gcccaaatct tgtgacaaaa ctcacacatg cccaccgtgc ccagcacctg aactcctggg     1560
gggaccgtca gtcttcctct tccccccaaa acccaaggac accctcatga tctcccggac     1620
ccctgaggtc acatgcgtgg tggtggacgt gagccacgaa gaccctgagg tcaagttcaa     1680
ctggtacgtg gacggcgtgg aggtgcataa tgccaagaca aagccgcggg aggagcagta     1740
caacagcacg taccgggtgg tcagcgtcct caccgtcctg caccaggact ggctgaatgg     1800
caaggagtac aagtgcaagg tctccaacaa agccctccca gcccccatcg agaaaaccat     1860
ctccaaagcc aaagggcagc ccgagaacc acaggtgtac accctgcccc catcccggga     1920
tgagctgacc aagaaccagg tcagcctgac ctgcctggtc aaaggcttct atcccagcga     1980
catcgccgtg gagtgggaga gcaatgggca gccggagaac aactacaaga ccacgcctcc     2040
cgtgctggac tccgacggct ccttcttcct ctacagcaag ctcaccgtgg acaagagcag     2100
gtggcagcag gggaacgtct tctcatgctc cgtgatgcat gaggctctgc acaaccacta     2160
cacgcagaag agcctctccc tgtctccggg taaattttgg gtgctggtgg tggttggtgg     2220
agtcctggct tgctatagct tgctagtaac agtggccttt attattttct gggtgaggag     2280
taagaggagc aggctcctgc acagtgacta catgaacatg actccccgcc gccccgggcc     2340
cacccgcaag cattaccagc cctatgcccc accacgcgac ttcgcagcct atcgctccgc     2400
cctgtacctg ctccggaggg accagaggct gcccccccgat gcccacaagc ccctgggggg     2460
aggcagtttc cggaccccca tccaagagga gcaggccgac gcccactcca ccctggccaa     2520
gatcagagtg aaaattcagc ggagcgcaga cgccccgcg taccagcagg gccagaacca     2580
gctctataac gagctcaatc taggacgaag agaggagtac gatgttttgg acaagagacg     2640
tggccgggac cctgagatgg ggggaaagcc gcagagaagg aagaaccctc aggaaggcct     2700
gtacaatgaa ctgcagaaag ataagatggc ggaggcctac agtgagattg ggatgaaagg     2760
cgagcgccgg aggggcaagg ggcacgatgg cctttaccag ggtctcagta cagccaccaa     2820
ggacacctac gacgcccttc acatgcaggc cctgccccct cgccatcatc accatcacca     2880
ttaa                                                                 2884

<210> SEQ ID NO 10
<211> LENGTH: 3469
<212> TYPE: DNA
<213> ORGANISM: Artificial Sequence
```

<220> FEATURE:
<223> OTHER INFORMATION: CMV-CTLA4 Rib48-CAR sequence

<400> SEQUENCE: 10

| | | | | | |
|---|---|---|---|---|---|
| gttgacattg | attattgact | agtuattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtacgcccc | ctattgacgt | caatgacggt | aaatggcccg | 300 |
| cctggcatta | tgcccagtac | atgaccttat | gggactttcc | tacttggcag | tacatctacg | 360 |
| tattagtcat | cgctattacc | atggtgatgc | ggttttggca | gtacatcaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | caactccgcc | ccattgacgc | 540 |
| aaatgggcgg | taggcgtgta | cggtgggagg | tctatataag | cagagctctc | tggctaacta | 600 |
| gagaacccac | tgcttactgg | cttatcgaaa | ttaatacgac | tcactatagg | gagacccaag | 660 |
| ctggctagcg | tttaaactta | agcttaaagc | ttatcctatg | gatagaaaag | ttatcaggca | 720 |
| tgcacctggt | agctagtctt | taaaccaata | gattgcatcg | gtttaaaagg | caagaccgtc | 780 |
| aaattgcggg | aaaggggtca | acagccgttc | agtaccaagt | ctcaggggaa | actttgagat | 840 |
| ggccttgcaa | agggtatggt | aataagctga | cggacatggt | cctaaccacg | cagccaagtc | 900 |
| ctaagtcaac | agatcttctg | ttgatatgga | tgcagttcac | agactaaatg | tcggtcgggg | 960 |
| aagatgtatt | cttctcataa | gatatagtcg | gacctctcct | taatgggagc | tagcggatga | 1020 |
| agtgatgcaa | cactggagcc | gctgggaact | aatttgtatg | cgaaagtata | ttgattagtt | 1080 |
| ttggagtact | cgttaggatg | gatccatgga | atggagctgg | gtctttctct | tcttcctgtc | 1140 |
| agtaactaca | ggtgtccact | cccaggtcca | gcttgtgcag | tctggggctg | aagtgaagaa | 1200 |
| gcctggggct | tcagtgaagg | tgtcctgcaa | ggcttctggc | tacaccttca | ctgaccatgc | 1260 |
| aattcactgg | gtgcgccagg | cccctggaca | acgccttgag | tggatgggat | atttttctcc | 1320 |
| tggcaacgat | gattttaaat | actcccagaa | gttccaggga | cgcgtgacaa | tcactgcgga | 1380 |
| caaatccgcg | agcacagcct | acatggagct | gagcagcctg | agatctgagg | acacggcggt | 1440 |
| ctattactgt | gcaagatcgt | ggatcatgca | gtactgggc | caagggactc | tggtcactgt | 1500 |
| ctcttcaggt | ggaggcggtt | caggcggagg | tggctctggc | ggtggcggat | cggacattgt | 1560 |
| gatgacccag | tctccagact | ccctggctgt | gtctctgggc | gagagggcca | ccatcaactg | 1620 |
| caagtccagc | cagagtgttt | tatacagcag | caacaataag | aactacttag | cttggtacca | 1680 |
| gcagaaacca | ggacagcctc | ctaagctgct | catttactgg | gcatctaccc | gggaatccgg | 1740 |
| ggtccctgac | cgattcagtg | gcagcgggtc | tgggacagat | ttcactctca | ccatcagcag | 1800 |
| cctgcaggct | gaagatgtgg | cagtttatta | ctgtcagcaa | tattattcct | atccgttgac | 1860 |
| gttcggccaa | gggaccaagg | tggaaatcaa | acgctggcca | ggttctccaa | aggcacaggc | 1920 |
| ctcctccgtg | cccactgcac | aaccccaagc | agagggcagc | ctcgccaagg | caaccacagc | 1980 |
| cccagccacc | acccgtaaca | caggtagagg | aggagagag | aagaagaagg | agaaggagaa | 2040 |
| agaggaacaa | gaagagagag | agacaaagac | accaggttgt | ccggagccca | atcttgtga | 2100 |
| caaaactcac | acatgcccac | cgtgcccagc | acctgaactc | ctggggggac | cgtcagtctt | 2160 |
| cctcttcccc | ccaaaaccca | aggacaccct | catgatctcc | cggacccctg | aggtcacatg | 2220 |

| | |
|---|---|
| cgtggtggtg acgtgagcc acgaagaccc tgaggtcaag ttcaactggt acgtggacgg | 2280 |
| cgtggaggtg cataatgcca agacaaagcc gcgggaggag cagtacaaca gcacgtaccg | 2340 |
| ggtggtcagc gtcctcaccg tcctgcacca ggactggctg aatggcaagg agtacaagtg | 2400 |
| caaggtctcc aacaaagccc tcccagcccc catcgagaaa accatctcca aagccaaagg | 2460 |
| gcagcccga gaaccacagg tgtacaccct gcccccatcc cgggatgagc tgaccaagaa | 2520 |
| ccaggtcagc ctgacctgcc tggtcaaagg cttctatccc agcgacatcg ccgtggagtg | 2580 |
| ggagagcaat gggcagccgg agaacaacta caagaccacg cctcccgtgc tggactccga | 2640 |
| cggctccttc ttcctctaca gcaagctcac cgtggacaag agcaggtggc agcaggggaa | 2700 |
| cgtcttctca tgctccgtga tgcatgaggc tctgcacaac cactacacgc agaagagcct | 2760 |
| ctccctgtct ccgggtaaat tttgggtgct ggtggtggtt ggtggagtcc tggcttgcta | 2820 |
| tagcttgcta gtaacagtgg cctttattat tttctgggtg aggagtaaga ggagcaggct | 2880 |
| cctgcacagt gactacatga acatgactcc ccgccgcccc gggcccaccc gcaagcatta | 2940 |
| ccagccctat gccccaccac gcgacttcgc agcctatcgc tccgcccgt acctgctccg | 3000 |
| gagggaccag aggctgcccc ccgatgccca agcccccct gggggaggca gtttccggac | 3060 |
| ccccatccaa gaggagcagg ccgacgccca ctccaccctg ccaagatca gagtgaaatt | 3120 |
| cagcaggagc gcagacgccc ccgcgtacca gcagggccag aaccagctct ataacgagct | 3180 |
| caatctagga cgaagagagg agtacgatgt tttggacaag acgtggcc gggaccctga | 3240 |
| gatgggggga aagccgcaga gaaggaagaa ccctcaggaa ggcctgtaca atgaactgca | 3300 |
| gaaagataag atggcggagg cctacagtga gattgggatg aaaggcgagc gccggagggg | 3360 |
| caagggcac gatggccttt accagggtct cagtacagcc accaaggaca cctacgacgc | 3420 |
| ccttcacatg caggccctgc cccctcgcca tcatcaccat caccattaa | 3469 |

<210> SEQ ID NO 11
<211> LENGTH: 3569
<212> TYPE: DNA
<213> ORGANISM: Artificial Sequence
<220> FEATURE:
<223> OTHER INFORMATION: CMV-AS-CTLA4 Rib48-CAR sequence

<400> SEQUENCE: 11

| | |
|---|---|
| gttgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc tggctaacta | 600 |
| gagaacccac tgcttactgg cttatcgaaa ttaatacgac tcactatagg gagacccaag | 660 |
| ctggctagcg tttaaactta agcttagcca tggcttatg ggagcggtgt tcaggtcttc | 720 |
| aggaagtaga gcaaaacctt tcaggatcct gaagctttga aatgtgtttg aacccacaca | 780 |
| gaatcaaagc ttatcctatg gatagaaaag ttatcaggca tgcacctggt agctagtctt | 840 |

```
taaaccaata gattgcatcg gtttaaaagg caagaccgtc aaattgcggg aaagggtca       900
acagccgttc agtaccaagt ctcaggggaa actttgagat ggccttgcaa agggtatggt      960
aataagctga cggacatggt cctaaccacg cagccaagtc ctaagtcaac agatcttctg     1020
ttgatatgga tgcagttcac agactaaatg tcggtcgggg aagatgtatt cttctcataa     1080
gatatagtcg gacctctcct taatgggagc tagcggatga agtgatgcaa cactggagcc     1140
gctgggaact aatttgtatg cgaaagtata ttgattagtt ttggagtact cgttaggatg     1200
gatccatgga atggagctgg gtctttctct tcttcctgtc agtaactaca ggtgtccact     1260
cccaggtcca gcttgtgcag tctgggctg aagtgaagaa gcctgggct tcagtgaagg      1320
tgtcctgcaa ggcttctggc tacaccttca ctgaccatgc aattcactgg gtgcgccagg    1380
cccctggaca acgccttgag tggatgggat attttctcc tggcaacgat gattttaaat    1440
actcccagaa gttccaggga cgcgtgacaa tcactgcgga caaatccgcg agcacagcct     1500
acatggagct gagcagcctg agatctgagg acacggcgt ctattactgt gcaagatcgt      1560
ggatcatgca gtactggggc caagggactc tggtcactgt ctcttcaggt ggaggcggtt     1620
caggcggagg tggctctggc ggtggcggat cggacattgt gatgacccag tctccagact    1680
ccctggctgt gtctctgggc gagagggcca ccatcaactg caagtccagc cagagtgttt    1740
tatacagcag caacaataag aactacttag cttggtacca gcagaaacca ggacagcctc     1800
ctaagctgct catttactgg gcatctaccc gggaatccgg ggtccctgac cgattcagtg    1860
gcagcgggtc tgggacagat ttcactctca ccatcagcag cctgcaggct gaagatgtgg    1920
cagtttatta ctgtcagcaa tattattcct atccgttgac gttcggccaa gggaccaagg    1980
tggaaatcaa acgctggcca ggttctccaa aggcacaggc ctcctccgtg cccactgcac    2040
aaccccaagc agagggcagc ctcgccaagg caaccacagc cccagccacc acccgtaaca    2100
caggtagagg aggagaagag aagaagaagg agaaggagaa agaggaacaa gaagagagag    2160
agacaaagac accaggttgt ccggagccca atcttgtga caaaactcac acatgcccac     2220
cgtgcccagc acctgaactc ctgggggac cgtcagtctt cctcttcccc ccaaaaccca     2280
aggacaccct catgatctcc cggacccctg aggtcacatg cgtggtggtg gacgtgagcc    2340
acgaagaccc tgaggtcaag ttcaactggt acgtggacgg cgtggaggtg cataatgcca    2400
agacaaagcc gcgggaggag cagtacaaca gcacgtaccg ggtggtcagc gtcctcaccg    2460
tcctgcacca ggactggctg aatggcaagg agtacaagtg caaggtctcc aacaaagccc    2520
tcccagcccc catcgagaaa accatctcca aagccaaagg gcagcccga gaaccacagg     2580
tgtacaccct gcccccatcc cgggatgagc tgaccaagaa ccaggtcagc ctgacctgcc    2640
tggtcaaagg cttctatccc agcgacatcg ccgtggagtg ggagagcaat gggcagccgg    2700
agaacaacta caagaccacg cctcccgtgc tggactccga cggctccttc ttcctctaca    2760
gcaagctcac cgtggacaag agcaggtggc agcaggggaa cgtcttctca tgctccgtga    2820
tgcatgaggc tctgcacaac cactacacgc agaagagcct ctccctgtct ccgggtaaat    2880
tttgggtgct ggtggtggtt ggtggagtcc tggcttgcta tagcttgcta gtaacagtgg    2940
cctttattat tttctgggtg aggagtaaga ggagcaggct cctgcacagt gactactatga   3000
acatgactcc ccgccgcccc gggcccaccc gcaagcatta ccagccctat gccccaccac    3060
gcgacttcgc agcctatcgc tccgccctgt acctgctccg gagggaccag aggctgcccc    3120
ccgatgccca caagccccct gggggaggca gtttccggac cccatccaa gaggagcagg     3180
```

| | |
|---|---|
| ccgacgccca ctccaccctg gccaagatca gagtgaaatt cagcaggagc gcagacgccc | 3240 |
| ccgcgtacca gcagggccag aaccagctct ataacgagct caatctagga cgaagagagg | 3300 |
| agtacgatgt tttggacaag agacgtggcc gggaccctga gatgggggga aagccgcaga | 3360 |
| gaaggaagaa ccctcaggaa ggcctgtaca atgaactgca gaaagataag atggcggagg | 3420 |
| cctacagtga gattgggatg aaaggcgagc gccggagggg caaggggcac gatggccttt | 3480 |
| accagggtct cagtcagcc accaaggaca cctacgacgc ccttcacatg caggccctgc | 3540 |
| cccctcgcca tcatcaccat caccattaa | 3569 |

<210> SEQ ID NO 12
<211> LENGTH: 1656
<212> TYPE: DNA
<213> ORGANISM: Artificial Sequence
<220> FEATURE:
<223> OTHER INFORMATION: F.luciferase

<400> SEQUENCE: 12

| | |
|---|---|
| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct agtaccaacc ctattttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc attttttgaa gcgaaggttg tggatctgga taccgggaaa | 1140 |
| acgctgggcg ttaatcagag aggcgaatta tgtgtcagag gacctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga aagacgatga cggaaaaaga tcgtggat | 1500 |
| tacgtggcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gtccaaattg taataa | 1656 |

<210> SEQ ID NO 13
<211> LENGTH: 2075
<212> TYPE: DNA
<213> ORGANISM: Artificial Sequence
<220> FEATURE:
<223> OTHER INFORMATION: IGS48P1P10-F.luci sequence

<400> SEQUENCE: 13

| | | | | | |
|---|---|---|---|---|---|
| agcttatcct | atggatagaa | aagttatcag | gcatgcacct | ggtagctagt | ctttaaacca | 60 |
| atagattgca | tcggtttaaa | aggcaagacc | gtcaaattgc | gggaaagggg | tcaacagccg | 120 |
| ttcagtacca | agtctcaggg | gaaactttga | gatggccttg | caaagggtat | ggtaataagc | 180 |
| tgacggacat | ggtcctaacc | acgcagccaa | gtcctaagtc | aacagatctt | ctgttgatat | 240 |
| ggatgcagtt | cacagactaa | atgtcggtcg | gggaagatgt | attcttctca | taagatatag | 300 |
| tcggacctct | ccttaatggg | agctagcgga | tgaagtgatg | caacactgga | gccgctggga | 360 |
| actaatttgt | atgcgaaagt | atattgatta | gttttggagt | actcgttagg | atgcccacca | 420 |
| tggaagacgc | caaaaacata | agaaaggcc | cggcgccatt | ctatcctcta | gaggatggaa | 480 |
| ccgctggaga | gcaactgcat | aaggctatga | agagatacgc | cctggttcct | ggaacaattg | 540 |
| cttttacaga | tgcacatatc | gaggtgaaca | tcacgtacgc | ggaatacttc | gaaatgtccg | 600 |
| ttcggttggc | agaagctatg | aaacgatatg | ggctgaatac | aaatcacaga | atcgtcgtat | 660 |
| gcagtgaaaa | ctctcttcaa | ttctttatgc | cggtgttggg | cgcgttattt | atcggagttg | 720 |
| cagttgcgcc | cgcgaacgac | atttataatg | aacgtgaatt | gctcaacagt | atgaacattt | 780 |
| cgcagcctac | cgtagtgttt | gtttccaaaa | aggggttgca | aaaaattttg | aacgtgcaaa | 840 |
| aaaaattacc | aataatccag | aaaattatta | tcatggattc | taaaacggat | taccagggat | 900 |
| ttcagtcgat | gtacacgttc | gtcacatctc | atctacctcc | cggttttaat | gaatacgatt | 960 |
| ttgtaccaga | gtcctttgat | cgtgacaaaa | caattgcact | gataatgaat | tcctctggat | 1020 |
| ctactgggtt | acctaagggt | gtggcccttc | cgcatagaac | tgcctgcgtc | agattctcgc | 1080 |
| atgccagaga | tcctattttt | ggcaatcaaa | tcattccgga | tactgcgatt | ttaagtgttg | 1140 |
| ttccattcca | tcacggtttt | ggaatgttta | ctacactcgg | atatttgata | tgtggatttc | 1200 |
| gagtcgtctt | aatgtataga | tttgaagaag | agctgttttt | acgatccctt | caggattaca | 1260 |
| aaattcaaag | tgcgttgcta | gtaccaaccc | tatttcatt | cttcgccaaa | agcactctga | 1320 |
| ttgacaaata | cgatttatct | aatttacacg | aaattgcttc | tgggggcgca | cctctttcga | 1380 |
| aagaagtcgg | ggaagcggtt | gcaaaacgct | tccatcttcc | agggatacga | caaggatatg | 1440 |
| ggctcactga | gactacatca | gctattctga | ttacacccga | gggggatgat | aaaccgggcg | 1500 |
| cggtcggtaa | agttgttcca | ttttttgaag | cgaaggttgt | ggatctggat | accgggaaaa | 1560 |
| cgctgggcgt | taatcagaga | ggcgaattat | gtgtcagagg | acctatgatt | atgtccggtt | 1620 |
| atgtaaacaa | tccggaagcg | accaacgcct | tgattgacaa | ggatggatgg | ctacattctg | 1680 |
| gagacatagc | ttactgggac | gaagacgaac | acttcttcat | agttgaccgc | ttgaagtctt | 1740 |
| taattaaata | caaaggatat | caggtggccc | ccgctgaatt | ggaatcgata | ttgttacaac | 1800 |
| accccaacat | cttcgacgcg | ggcgtggcag | gtcttcccga | cgatgacgcc | ggtgaacttc | 1860 |
| ccgccgccgt | tgttgttttg | gagcacggaa | agacgatgac | ggaaaaagag | atcgtggatt | 1920 |
| acgtggccag | tcaagtaaca | accgcgaaaa | agttgcgcgg | aggagttgtg | tttgtggacg | 1980 |
| aagtaccgaa | aggtcttacc | ggaaaactcg | acgcaagaaa | aatcagagag | atcctcataa | 2040 |

```
aggccaagaa gggcggaaag tccaaattgt aataa                               2075
```

<210> SEQ ID NO 14
<211> LENGTH: 3845
<212> TYPE: DNA
<213> ORGANISM: Artificial Sequence
<220> FEATURE:
<223> OTHER INFORMATION: AS100-IGS48P1P10-F.luci sequence

<400> SEQUENCE: 14

```
agccatggct ttatgggagc ggtgttcagg tcttcaggaa gtagagcaaa acctttcagg    60
atcctgaagc tttgaaatgt gtttgaaccc acacagaatc aaagcttatc ctatggatag   120
aaaagttatc aggcatgcac ctggtagcta gtctttaaac caatagattg catcggttta   180
aaaggcaaga ccgtcaaatt gcgggaaagg ggtcaacagc cgttcagtac caagtctcag   240
gggaaacttt gagatggcct tgcaaagggt atggtaataa gctgacggac atggtcctaa   300
ccacgcagcc aagtcctaag tcaacagatc ttctgttgat atggatgcag ttcacagact   360
aaatgtcggt cggggaagat gtattcttct cataagatat agtcggacct ctccttaatg   420
ggagctagcg gatgaagtga tgcaacactg gagccgctgg gaactaattt gtatgcgaaa   480
gtatattgat tagttttgga gtactcgtta ggatgcccac catggaagac gccaaaaaca   540
taaagaaagg cccggcgcca ttctatcctc tagaggatgg aaccgctgga gagcaactgc   600
ataaggctat gaagagatac gccctggttc ctggaacaat tucrasgctt ttacagatgc   660
acatatcgag gtgaacatca cgtacgcgga atacttcgaa atgtccgttc ggttggcaga   720
agctatgaaa cgatatgggc tgaatacaaa tcacagaatc gtcgtatgca gtgaaaactc   780
tcttcaattc tttatgccgg tgttgggcgc gttatttatc ggagttgcag ttgcgcccgc   840
gaacgacatt tataatgaac gtgaattgct caacagtatg aacatttcgc agcctaccgt   900
agtgtttgtt tccaaaaagg ggttgcaaaa aattttgaac gtgcaaaaaa attaccaat    960
aatccagaaa attattatca tggattctaa aacggattac cagggatttc agtcgatgta  1020
cacgttcgtc acatctcatc tacctcccgg ttttaatgaa tacgattttg taccagagtc  1080
ctttgatcgt gacaaaacaa ttgcactgat aatgaattcc tctggatcta ctgggttacc  1140
taagggtgtg gcccttccgc atagaactgc ctgcgtcaga ttctcgcatg ccagagatcc  1200
tattttttggc aatcaaatca ttccggatac tgcgatttta agtgttgttc cattccatca  1260
cggttttgga atgtttacta cactcggata tttgatatgt ggatttcgag tcgtcttaat  1320
gtatagattt gaagaagagc tgtttttacg atcccttcag gattacaaaa ttcaaagtgc  1380
gttgctagta ccaaccctat tttcattctt cgccaaaagc actctgattg acaaatacga  1440
tttatctaat ttacacgaaa ttgcttctgg gggcgcacct ctttcgaaag aagtcgggga  1500
agcggttgca aaacgcttcc atcttccagg gatacgacaa ggatatgggc tcactgagac  1560
tacatcagct attctgatta cacccgaggg ggatgataaa ccgggcgcgg tcggtaaagt  1620
tgttccattt tttgaagcga aggttgtgga tctggatacc gggaaaacgc tgggcgttaa  1680
tcagagaggc gaattatgtg tcagaggacc tatgattatg tccggttatg taaacaatcc  1740
ggaagcgacc aacgccttga ttgacaagga tggatggcta cattctggag acatagctta  1800
ctgggacgaa gacgaacact tcttcatagt tgaccgcttg aagtctttaa ttaaatacaa  1860
aggatatcag gtggccccg ctgaattgga atcgatattg ttacaacacc ccaacatctt  1920
cgacgcgggc gtggcaggtc ttcccgacga tgacgccggt gaacttcccg ccgccgttgt  1980
tgttttggag cacggaaaga cgatgacgga aaaagagatc gtggattacg tggccagtca  2040
```

```
agtaacaacc gcgaaaaagt tgcgcggagg agttgtgttt gtggacgaag taccgaaagg    2100
tcttaccgga aaactcgacg caagaaaaat cagagagatc ctcataaagg ccaagaaggg    2160
cggaaagtcc aaattgtaat aagcccacca tggaagacgc caaaaacata agaaaggcc    2220 cggcgccatt ctatcctcta gaggatggaa ccgctggaga gcaactgcat aaggctatga    2280
agagatacgc cctggttcct ggaacaattg cttttacaga tgcacatatc gaggtgaaca    2340
tcacgtacgc ggaatacttc gaaatgtccg ttcggttggc agaagctatg aaacgatatg    2400
ggctgaatac aaatcacaga atcgtcgtat gcagtgaaaa ctctcttcaa ttctttatgc    2460
cggtgttggg cgcgttattt atcggagttg cagttgcgcc cgcgaacgac atttataatg    2520
aacgtgaatt gctcaacagt atgaacattt cgcagcctac cgtagtgttt gtttccaaaa    2580
aggggttgca aaaattttg aacgtgcaaa aaaaattacc aataatccag aaaattatta    2640
tcatggattc taaaacggat taccagggat ttcagtcgat gtacacgttc gtcacatctc    2700
atctacctcc cggttttaat gaatacgatt ttgtaccaga gtcctttgat cgtgacaaaa    2760
caattgcact gataatgaat tcctctggat ctactgggtt acctaagggt gtggcccttc    2820
cgcatagaac tgcctgcgtc agattctcgc atgccagaga tcctatttt ggcaatcaaa    2880 tcattccgga tactgcgatt ttaagtgttg ttccattcca tcacggtttt ggaatgttta    2940
ctacactcgg atatttgata tgtggatttc gagtcgtctt aatgtataga tttgaagaag    3000
agctgttttt acgatcccct caggattaca aaattcaaag tgcgttgcta gtaccaaccc    3060 tatttcatt cttcgccaaa agcactctga ttgacaaata cgatttatct aatttacacg    3120
aaattgcttc tgggggcgca cctctttcga agaagtcgg ggaagcggtt gcaaaacgct    3180
tccatcttcc agggatacga caaggatatg ggctcactga gactacatca gctattctga    3240
ttacacccga ggggatgat aaaccgggcg cggtcggtaa agttgttcca tttttgaag    3300 cgaaggttgt ggatctggat accgggaaaa cgctgggcgt taatcagaga ggcgaattat    3360
gtgtcagagg acctatgatt atgtccggtt atgtaaacaa tccggaagcg accaacgcct    3420
tgattgacaa ggatggatgg ctacattctg gagacatagc ttactgggac gaagacgaac    3480
acttcttcat agttgaccgc ttgaagtctt taattaaata caaaggatat caggtggccc    3540
ccgctgaatt ggaatcgata ttgttacaac accccaacat cttcgacgcg gcgtggcag    3600 gtcttcccga cgatgacgcc ggtgaacttc ccgccgccgt tgttgttttg gagcacggaa    3660
agacgatgac ggaaaaagag atcgtggatt acgtggccag tcaagtaaca accgcgaaaa    3720 agttgcgcg aggagttgtg tttgtggacg aagtaccgaa aggtcttacc ggaaaactcg    3780
acgcaagaaa aatcagagag atcctcataa aggccaagaa gggcggaaag tccaaattgt    3840
aataa                                                                3845
```

<210> SEQ ID NO 15
<211> LENGTH: 2377
<212> TYPE: DNA
<213> ORGANISM: Artificial Sequence
<220> FEATURE:
<223> OTHER INFORMATION: AS300-IGS48P1P10-F.luci sequence

<400> SEQUENCE: 15

```
acctcagtgg ctttgcctgg agatgcatac tcacacacaa agctggcgat gcctcggctg      60
ctggccagta ccacagcagg ctgggccacg tgcattgctt tgcagaagac agggatgaag     120
agaagaaaaa acaggagagt gcagggccag gtcctggtag ccaggttcag ctgagccttg     180
```

```
tgccgctgaa atccaaggca agccatggct ttatgggagc ggtgttcagg tcttcaggaa    240
gtagagcaaa acctttcagg atcctgaagc tttgaaatgt gtttgaaccc acacagaatc    300
aaagcttatc ctatggatag aaaagttatc aggcatgcac ctggtagcta gtctttaaac    360
caatagattg catcggttta aaaggcaaga ccgtcaaatt gcgggaaagg ggtcaacagc    420
cgttcagtac caagtctcag gggaaacttt gagatggcct tgcaaagggt atggtaataa    480
gctgacggac atggtcctaa ccacgcagcc aagtcctaag tcaacagatc ttctgttgat    540
atggatgcag ttcacagact aaatgtcggt cggggaagat gtattcttct cataagatat    600
agtcggacct ctccttaatg ggagctagcg gatgaagtga tgcaacactg gagccgctgg    660
gaactaattt gtatgcgaaa gtatattgat tagttttgga gtactcgtta ggatgcccac    720
catgaaagac gccaaaaaca taagaaaagg cccggcgcca ttctatcctc tagaggatgg    780
aaccgctgga gagcaactgc ataaggctat gaagagatac gccctggttc ctggaacaat    840
tgcttttaca gatgcacata tcgaggtgaa catcacgtac gcggaatact tcgaaatgtc    900
cgttcggttg gcagaagcta tgaaacgata tgggctgaat acaaatcaca gaatcgtcgt    960
atgcagtgaa aactctcttc aattctttat gccggtgttg ggcgcgttat ttatcggagt   1020
tgcagttgcg cccgcgaacg acattttataa tgaacgtgaa ttgctcaaca gtatgaacat   1080
ttcgcagcct accgtagtgt ttgttttccaa aaggggttg caaaaatttt gaacgtgca    1140 aaaaaaatta ccaataatcc agaaaattat tatcatggat tctaaaacgg attaccaggg   1200
atttcagtcg atgtacacgt tcgtcacatc tcatctacct cccggtttta atgaatacga   1260
ttttgtacca gagtcctttg atcgtgacaa acaattgca ctgataatga attcctctgg    1320
atctactggg ttacctaagg gtgtggccct tccgcataga actgcctgcg tcagattctc   1380
gcatgccaga gatcctattt ttggcaatca aatcattccg gatactgcga ttttaagtgt   1440
tgttccattc catcacggtt ttggaatgtt tactacactc ggatatttga tatgtggatt   1500
tcgagtcgtc ttaatgtata gatttgaaga agagctgttt ttacgatccc ttcaggatta   1560
caaaattcaa agtgcgttgc tagtaccaac cctattttca ttcttcgcca aaagcactct   1620
gattgacaaa tacgatttat ctaatttaca cgaaattgct tctggggcg caccctcttt   1680 gaaagaagtc ggggaagcgg ttgcaaaacg cttccatctt ccagggatac gacaaggata   1740
tgggctcact gagactacat cagctattct gattacaccc gagggggatg ataaaccggg   1800
cgcggtcggt aaagttgttc catttttga agcgaaggtt gtggatctgg ataccgggaa   1860
aacgctgggc gttaatcaga gaggcgaatt atgtgtcaga ggacctatga ttatgtccgg   1920
ttatgtaaac aatccggaag cgaccaacgc cttgattgac aaggatggat ggctacattc   1980
tggagacata gcttactggg acgaagacga acacttcttc atagttgacc gcttgaagtc   2040
tttaattaaa tacaaaggat atcaggtggc ccccgctgaa ttggaatcga tattgttaca   2100
acaccccaac atcttcgacg cgggcgtggc aggtcttccc gacgatgacg ccggtgaact   2160
tcccgccgcc gttgttgttt tggagcacgg aaagacgatg acggaaaaag agatcgtgga   2220
ttacgtggcc agtcaagtaa caaccgcgaa aaagttgcgc ggaggagttg tgtttgtgga   2280
cgaagtaccg aaaggtctta ccggaaaact cgacgcaaga aaaatcagag agatcctcat   2340
aaaggccaag aagggcggaa agtccaaatt gtaataa                            2377
```

<210> SEQ ID NO 16
<211> LENGTH: 2066
<212> TYPE: DNA
<213> ORGANISM: Artificial Sequence
<220> FEATURE:
<223> OTHER INFORMATION: IGS111P1P10-F.luci sequence

<400> SEQUENCE: 16

```
tttgccttta aaagttatca ggcatgcacc tggtagctag tctttaaacc aatagattgc      60
atcggtttaa aaggcaagac cgtcaaattg cgggaaaggg gtcaacagcc gttcagtacc     120
aagtctcagg ggaaactttg agatggcctt gcaaagggta tggtaataag ctgacggaca     180
tggtcctaac cacgcagcca agtcctaagt caacagatct tctgttgata tggatgcagt     240
tcacagacta aatgtcggtc ggggaagatg tattcttctc ataagatata gtcggacctc     300
tccttaatgg gagctagcgg atgaagtgat gcaacactgg agccgctggg aactaatttg     360
tatgcgaaag tatattgatt agttttggag tactcgtaag gatgcccacc atggaagacg     420
ccaaaaacat aaagaaaggc ccggcgccat tctatcctct agaggatgga accgctggag     480
agcaactgca taaggctatg aagagatacg ccctggttcc tggaacaatt gcttttacag     540
atgcacatat cgaggtgaac atcacgtacg cggaatactt cgaaatgtcc gttcggttgg     600
cagaagctat gaaacgatat gggctgaata caaatcacag aatcgtcgta tgcagtgaaa     660
actctcttca attctttatg ccggtgttgg gcgcgttatt tatcggagtt gcagttgcgc     720
ccgcgaacga catttataat gaacgtgaat tgctcaacag tatgaacatt tcgcagccta     780
ccgtagtgtt tgtttccaaa aaggggttgc aaaaaatttt gaacgtgcaa aaaaattac      840
caataatcca gaaaattatt atcatggatt ctaaaacgga ttaccaggga tttcagtcga     900
tgtacacgtt cgtcacatct catctacctc ccggttttaa tgaatacgat tttgtaccag     960
agtcctttga tcgtgacaaa acaattgcac tgataatgaa ttcctctgga tctactgggt    1020
tacctaaggg tgtggccctt ccgcatagaa ctgcctgcgt cagattctcg catgccagag    1080
atcctatttt tggcaatcaa atcattccgg atactgcgat tttaagtgtt gttccattcc    1140
atcacggttt tggaatgttt actacactcg gatatttgat atgtggattt cgagtcgtct    1200
taatgtatag atttgaagaa gagctgtttt tacgatccct tcaggattac aaaattcaaa    1260
gtgcgttgct agtaccaacc ctattttcat tcttcgccaa aagcactctg attgacaaat    1320
acgatttatc taatttacac gaaattgctt ctggggcgc acctctttcg aaagaagtcg    1380
gggaagcggt tgcaaaacgc ttccatcttc cagggatacg acaaggatat gggctcactg    1440
agactacatc agctattctg attacacccg aggggatga taaaccgggc gcggtcggta    1500
aagttgttcc attttttgaa gcgaaggttg tggatctgga taccgggaaa acgctgggcg    1560
ttaatcagag aggcgaatta tgtgtcagag gacctatgat tatgtccggt tatgtaaaca    1620
atccggaagc gaccaacgcc ttgattgaca aggatggatg gctacattct ggagacatag    1680
cttactggga cgaagacgaa cacttcttca tagttgaccg cttgaagtct ttaattaaat    1740
acaaaggata tcaggtggcc cccgctgaat tggaatcgat attgttacaa cacccccaaca    1800
tcttcgacgc gggcgtggca ggtcttcccg acgatgacgc cggtgaactt cccgccgccg    1860
ttgttgtttt ggagcacgga aagacgatga cggaaaaaga gatcgtggat tacgtggcca    1920
gtcaagtaac aaccgcgaaa aagttgcgcg gaggagttgt gtttgtggac gaagtaccga    1980
aaggtcttac cggaaaactc gacgcaagaa aaatcagaga gatcctcata aaggccaaga    2040
agggcggaaa gtccaaattg taataa                                         2066
```

<210> SEQ ID NO 17
<211> LENGTH: 2076
<212> TYPE: DNA

<213> ORGANISM: Artificial Sequence
<220> FEATURE:
<223> OTHER INFORMATION: IGS232P1P10-F.luci sequence

<400> SEQUENCE: 17

```
agcttatcct tgacaggaa aagttatcag gcatgcacct ggtagctagt ctttaaacca      60
atagattgca tcggtttaaa aggcaagacc gtcaaattgc gggaaagggg tcaacagccg     120
ttcagtacca agtctcaggg gaaactttga gatggccttg caagggtat ggtaataagc     180
tgacggacat ggtcctaacc acgcagccaa gtcctaagtc aacagatctt ctgttgatat    240
ggatgcagtt cacagactaa atgtcggtcg gggaagatgt attcttctca taagatatag    300
tcggacctct ccttaatggg agctagcgga tgaagtgatg caacactgga gccgctggga    360
actaatttgt atgcgaaagt atattgatta gttttggagt actgtaagga tgcccaccac    420
atggaagacg ccaaaaacat aaagaaaggc ccggcgccat tctatcctct agaggatgga    480
accgctggag agcaactgca taaggctatg aagagatacg ccctggttcc tggaacaatt    540
gcttttacag atgcacatat cgaggtgaac atcacgtacg cggaatactt cgaaatgtcc    600
gttcggttgg cagaagctat gaaacgatat gggctgaata caaatcacag aatcgtcgta    660
tgcagtgaaa actctcttca attctttatg ccggtgttgg gcgcgttatt tatcggagtt    720
gcagttgcgc ccgcgaacga catttataat gaacgtgaat tgctcaacag tatgaacatt    780
tcgcagccta ccgtagtgtt tgtttccaaa aaggggttgc aaaaaatttt gaacgtgcaa    840
aaaaaattac caataatcca gaaaattatt atcatggatt ctaaaacgga ttaccaggga    900
tttcagtcga tgtacacgtt cgtcacatct catctacctc ccggttttaa tgaatacgat    960
tttgtaccag agtcctttga tcgtgacaaa acaattgcac tgataatgaa ttcctctgga   1020
tctactgggt tacctaaggg tgtggccctt ccgcatagaa ctgcctgcgt cagattctcg   1080
catgccagag atcctatttt tggcaatcaa atcattccgg atactgcgat tttaagtgtt   1140
gttccattcc atcacggttt tggaatgttt actacactcg atatttgat atgtggattt   1200
cgagtcgtct taatgtatag atttgaagaa gagctgtttt tacgatccct tcaggattac   1260
aaaattcaaa gtgcgttgct agtaccaacc ctattttcat tcttcgccaa agcactctg   1320
attgacaaat acgatttatc taatttacac gaaattgctt ctgggggcgc acctctttcg   1380
aaagaagtcg gggaagcggt tgcaaaacgc ttccatcttc cagggatacg acaaggatat   1440
gggctcactg agactacatc agctattctg attacacccg aggggatga taaaccgggc   1500
gcggtcggta aagttgttcc attttttgaa gcgaaggttg tggatctgga taccgggaaa   1560
acgctgggcg ttaatcagag aggcgaatta tgtgtcagag gacctatgat tatgtccggt   1620
tatgtaaaca atccggaagc gaccaacgcc ttgattgaca aggatggatg gctacattct   1680
ggagacatag cttactggga cgaagacgaa cacttcttca tagttgaccg cttgaagtct   1740
ttaattaaat acaaaggata tcaggtggcc cccgctgaat tggaatcgat attgttacaa   1800
caccccaaca tcttcgacgc gggcgtggca ggtcttcccg acgatgacgc cggtgaactt   1860
cccgccgccg ttgttgtttt ggagcacgga aagacgatga cggaaaaaga tcgtggat   1920
tacgtggcca gtcaagtaac aaccgcgaaa aagttgcgcg gaggagttgt gtttgtggac   1980
gaagtaccga aaggtcttac cggaaaactc gacgcaagaa aaatcagaga gatcctcata   2040
aaggccaaga agggcggaaa gtccaaattg taataa                              2076
```

<210> SEQ ID NO 18
<211> LENGTH: 18

```
<212> TYPE: DNA
<213> ORGANISM: Artificial Sequence
<220> FEATURE:
<223> OTHER INFORMATION: RY-RT primer

<400> SEQUENCE: 18
atgtgctgca aggcgatt                                                  18

<210> SEQ ID NO 19
<211> LENGTH: 19
<212> TYPE: DNA
<213> ORGANISM: Artificial Sequence
<220> FEATURE:
<223> OTHER INFORMATION: RY-TS primer

<400> SEQUENCE: 19
tgtaaaacga cggccagtg                                                 19

<210> SEQ ID NO 20
<211> LENGTH: 27
<212> TYPE: DNA
<213> ORGANISM: Artificial Sequence
<220> FEATURE:
<223> OTHER INFORMATION: CTLA4 5' UTR XhoI primer

<400> SEQUENCE: 20
ccgctcgagc ttctgtgtgt gcacatg                                        27

<210> SEQ ID NO 21
<211> LENGTH: 37
<212> TYPE: DNA
<213> ORGANISM: Artificial Sequence
<220> FEATURE:
<223> OTHER INFORMATION: IGS48P1P10 StuI primer

<400> SEQUENCE: 21
gaaggcctat cctatggata gaaaagttat caggcat                             37

<210> SEQ ID NO 22
<211> LENGTH: 37
<212> TYPE: DNA
<213> ORGANISM: Artificial Sequence
<220> FEATURE:
<223> OTHER INFORMATION: IGS111P1P10 StuI primer

<400> SEQUENCE: 22
gaaggcctat cctttgcctt taaaagttat caggcat                             37

<210> SEQ ID NO 23
<211> LENGTH: 37
<212> TYPE: DNA
<213> ORGANISM: Artificial Sequence
<220> FEATURE:
<223> OTHER INFORMATION: IGS232P1P10 StuI primer

<400> SEQUENCE: 23
gaaggcctat cctttgacag gaaaagttat caggcat                             37

<210> SEQ ID NO 24
<211> LENGTH: 46
<212> TYPE: DNA
<213> ORGANISM: Artificial Sequence
<220> FEATURE:
<223> OTHER INFORMATION: 5' F.luci ScaI P10 IGS48  primer

<400> SEQUENCE: 24
```
aaaagtactc gttaggatgc ccaccatgga agacgccaaa aacata        46

<210> SEQ ID NO 25
<211> LENGTH: 46
<212> TYPE: DNA
<213> ORGANISM: Artificial Sequence
<220> FEATURE:
<223> OTHER INFORMATION: 5' F.luci ScaI P10 IGS111 primer

<400> SEQUENCE: 25
aaaagtactc gtaaggatgc ccaccatgga agacgccaaa aacata        46

<210> SEQ ID NO 26
<211> LENGTH: 44
<212> TYPE: DNA
<213> ORGANISM: Artificial Sequence
<220> FEATURE:
<223> OTHER INFORMATION: 5' F.luci ScaI P10 IGS232 primer

<400> SEQUENCE: 26
aaaagtactg taaggatgcc caccacgaag acgccaaaaa cata        44

<210> SEQ ID NO 27
<211> LENGTH: 38
<212> TYPE: DNA
<213> ORGANISM: Artificial Sequence
<220> FEATURE:
<223> OTHER INFORMATION: IGS48 P1P10 HindIII primer

<400> SEQUENCE: 27
cccaagctta tcctatggat agaaaagtta tcaggcat        38

<210> SEQ ID NO 28
<211> LENGTH: 38
<212> TYPE: DNA
<213> ORGANISM: Artificial Sequence
<220> FEATURE:
<223> OTHER INFORMATION: IGS111 P1P10 HindIII primer

<400> SEQUENCE: 28
cccaagctta tcctttgcct ttaaaagtta tcaggcat        38

<210> SEQ ID NO 29
<211> LENGTH: 38
<212> TYPE: DNA
<213> ORGANISM: Artificial Sequence
<220> FEATURE:
<223> OTHER INFORMATION: IGS232 P1P10 HindIII primer

<400> SEQUENCE: 29
cccaagctta tcctttgaca ggaaaagtta tcaggcat        38

<210> SEQ ID NO 30
<211> LENGTH: 33
<212> TYPE: DNA
<213> ORGANISM: Artificial Sequence
<220> FEATURE:
<223> OTHER INFORMATION: 3' F.luci end XhoI primer

<400> SEQUENCE: 30
ccgctcgagt tacaatttgg actttccgcc ctt        33

<210> SEQ ID NO 31
<211> LENGTH: 35
<212> TYPE: DNA
<213> ORGANISM: Artificial Sequence

```
<220> FEATURE:
<223> OTHER INFORMATION: IGS48 AS100 kit F primer

<400> SEQUENCE: 31
cgtttaaact taagcttagc catggcttta tggga                              35

<210> SEQ ID NO 32
<211> LENGTH: 35
<212> TYPE: DNA
<213> ORGANISM: Artificial Sequence
<220> FEATURE:
<223> OTHER INFORMATION: IGS48 AS300 kit F primer

<400> SEQUENCE: 32
cgtttaaact taagcttacc tcagtggctt tgcct                              35

<210> SEQ ID NO 33
<211> LENGTH: 35
<212> TYPE: DNA
<213> ORGANISM: Artificial Sequence
<220> FEATURE:
<223> OTHER INFORMATION: IGS48 AS kit R primer

<400> SEQUENCE: 33
atggatccgc gaagctttga ttctgtgtgg gttca                              35

<210> SEQ ID NO 34
<211> LENGTH: 27
<212> TYPE: DNA
<213> ORGANISM: Artificial Sequence
<220> FEATURE:
<223> OTHER INFORMATION: IGS48 BamHI F primer

<400> SEQUENCE: 34
cgcggatcca tcctatggat agaaaag                                      27

<210> SEQ ID NO 35
<211> LENGTH: 27
<212> TYPE: DNA
<213> ORGANISM: Artificial Sequence
<220> FEATURE:
<223> OTHER INFORMATION: IGS48Rib BamHI R primer

<400> SEQUENCE: 35
cgcggatcca tcctaacgag tactcca                                      27

<210> SEQ ID NO 36
<211> LENGTH: 20
<212> TYPE: DNA
<213> ORGANISM: Artificial Sequence
<220> FEATURE:
<223> OTHER INFORMATION: CTLA4 real F primer

<400> SEQUENCE: 36
ctacctgggc ataggcaacg                                              20

<210> SEQ ID NO 37
<211> LENGTH: 20
<212> TYPE: DNA
<213> ORGANISM: Artificial Sequence
<220> FEATURE:
<223> OTHER INFORMATION: CTLA4 real R primer

<400> SEQUENCE: 37
ccccgaacta actgctgcaa                                              20
```

```
<210> SEQ ID NO 38
<211> LENGTH: 405
<212> TYPE: DNA
<213> ORGANISM: Artificial Sequence
<220> FEATURE:
<223> OTHER INFORMATION: CTLA-4 (IGS32) targeting ribozyme

<400> SEQUENCE: 38
ggatataaaa gttatcaggc atgcacctgg tagctagtct ttaaaccaat agattgcatc      60
ggtttaaaag gcaagaccgt caaattgcgg gaaaggggtc aacagccgtt cagtaccaag     120
tctcagggga aactttgaga tggccttgca aagggtatgg taataagctg acggacatgg     180
tcctaaccac gcagccaagt cctaagtcaa cagatcttct gttgatatgg atgcagttca     240
cagactaaat gtcggtcggg gaagatgtat tcttctcata agatatagtc ggacctctcc     300
ttaatgggag ctagcggatg aagtgatgca acactggagc cgctgggaac taatttgtat     360
gcgaaagtat attgattagt tttggagtac tcgtaaggta gccaa                     405
```

CTLA-4-TARGETING TRANS-SPLICING RIBOZYME FOR DELIVERY OF CHIMERIC ANTIGEN RECEPTOR, AND USE THEREOF

INCORPORATION BY REFERENCE OF MATERIAL SUBMITTED ELECTRONICALLY

Incorporated by reference in its entirety is a computer-readable nucleotide/amino acid sequence listing identified as follows: 47 kilobyte ASCII (Text) file named "Sequence_listing_52304.txt"; created on May 14, 2018.

TECHNICAL FIELD

The present invention relates to a recombinant vector, characterized by including a cytotoxic T-lymphocyte-associated protein-4 (CTLA-4)-targeting trans-splicing ribozyme expression cassette for delivery of chimeric antigen receptor, wherein the expression cassette includes: (i) a CTLA-4-targeting trans-splicing ribozyme; and (ii) a polynucleotide encoding a chimeric antigen receptor connected to the 3' exon of the ribozyme. The present invention also relates to a transformed cell into which the recombinant vector is introduced, a ribozyme expressed from the recombinant vector, a retrovirus expressing the ribozyme, and a T cell treated with the retrovirus. Furthermore, the present invention relates to a pharmaceutical composition for preventing or treating cancers, in which the pharmaceutical composition includes the recombinant vector, the transformed cell, the ribozyme, the retrovirus, the T cell, or a combination thereof; and a method for treating cancers, in which the method includes administering, to an individual in need thereof, the recombinant vector, the transformed cell, the ribozyme, the retrovirus, the T cell, or a combination thereof.

BACKGROUND ART

Cancer is a serious disease and the leading cause of human death. It may occur anywhere in the human body, and may be caused by various factors including environmental factor and genetic factor, etc. A large number of studies have been conducted to conquer cancer; however, cancer is an incurable disease that has not yet been conquered. Existing therapies against cancer include surgery, chemotherapy and radiotherapy, etc. Although advances in medicine have led to improved prognosis, there are many limitations related thereto, including normal cells being also adversely affected as well as cancer cells. In particular, most cancer therapies are currently implemented using surgical removal (surgery) or chemotherapy. In recent years, other therapies, which are based on a different concept from that of such existing therapies, have been studied, and particular interests are given to the studies which are intended to achieve effective treatment by selectively treating cancer tissues using an autoimmune system naturally present in the human body so as to minimize adverse effects.

It has been reported that cytotoxic T lymphocytes (CTLs), which directly target cancer cells, are important for effective treatment of cancer. To date, studies on anti-cancer treatment using T cell therapy have been attempted in a way that delivers, to T cells of a patient, either a T cell receptor (TCR) recognizing a specific antigen or a chimeric antigen receptor (CAR) in which an antibody's scFv portion recognizing an antigen is grafted to a CD3 signaling domain. Grafting of CAR to T cells allows to activate T cells to exert its anti-cancer effect with only recognition of a specific antigen by scFv regardless of signal transduction by an antigen presenting cell (APC), and also this is not limited to the HLA type, which, in turn, enables it to be used as an effective therapy. However, it has been developed largely as a therapeutic for hematologic cancers. In the case of solid cancers, CAR exhibited low therapeutic effects since an environment, which can suppress immunological actions, was created around cancer cells. Activation of T cells may induce the expression of a cytotoxic T-lymphocyte-associated protein-4 (CTLA-4), which binds to a ligand for regulatory T cell (Treg) that regulates the activity of activated T cells, and transduces an inhibitory signal into T cells, thereby leading to decreased activity of cancer-targeting T cells.

As used herein, the term "gene therapy" refers to a method of treating inherited or acquired genetic abnormalities, which are difficult to treat by conventional methods, using a genetic engineering method. Specifically, gene therapy includes administering genetic materials such as DNA and RNA into the human body to express therapeutic proteins or to inhibit the expression of specific proteins, thereby treating and preventing inherited or acquired genetic defects, viral diseases, or chronic diseases such as cancers or cardiovascular diseases. Gene therapy allows to fundamentally treat diseases by analyzing the cause of a disease on a genetic level, and thus is expected to not only overcome incurable diseases but also to be used as an alternative to conventional medical methods.

On the other hand, in recent years, studies have been conducted to develop a tissue-specific adenovirus for cancer therapy. As a typical example, a method using a trans-splicing ribozyme or the like is being developed.

Studies on the development of a tissue-specific adenovirus for cancer therapy using the trans-splicing ribozyme attracted interests by the revelation that the group I intron ribozyme from *Tetrahymena thermophila* can link two separately present transcripts to each other by a trans-splicing reaction, not only in vitro, but also in bacterial cells and even in human cells.

Specifically, this group I intron-based trans-splicing ribozyme can target a specific tissue- or disease-related gene transcript or a specific RNA that is specifically expressed only in diseased cells, thereby leading to reprogramming so that the RNA is repaired back to normal or the gene transcript is converted into a new therapeutic gene transcript. Thus, it is expected that the group I intron-based trans-splicing ribozyme can become a tissue or disease-specific and safe gene therapeutic technology. In addition, a trans-splicing ribozyme can multiply its therapeutic effects, because it allows a unusual RNA to be eliminated and, at the same time, expression of a desired therapeutic gene product to be induced, thereby achieving inhibition of a gene corresponding to a unusual RNA and induction of expression of a desired therapeutic gene.

Particularly, in recent studies, trans-splicing ribozymes have been developed, which target a gene capable of functioning specifically on cancer tissues such as human telomerase reverse transcriptase (hTERT); however, these ribozymes exhibit a high tissue specificity due to their combination with a tissue-specific promoter while exhibiting a very low expression efficiency. Thus, they still have a disadvantage to overcome in terms of the therapeutic efficiency.

In other words, gene therapy using a trans-splicing ribozyme has still been under continued research and development in order to improve the therapeutic efficiency.

On the other hand, many attempts have been made to achieve effective anti-cancer therapy using the existing immune system. By causing a T cell to express CAR which recognizes a specific antigen, a T cell directly attacking cancer cells has been developed without relying on APC. However, it has been developed largely as a therapeutic for hematologic cancers. In the case of solid cancers where an environment suppressing immunological actions is created around cancer tissue, it is known that CAR exhibits low therapeutic effects. In order to overcome this problem, attempts were made to maintain the activity of a T cell expressing CAR by inhibiting CLTA-4, which interferes with the activity of activated T cells, thereby achieving effective anti-cancer effects. However, according to previously reported studies, combined use of an anti-cancer drug and an antibody to CTLA-4 resulted in an overall inhibition of CTLA-4, thereby leading to low specificity and even adverse effects in terms of the anti-cancer effect.

DISCLOSURE

Technical Problem

All possible efforts have been made by the present inventors to develop a gene therapeutic approach for cancers which inhibits CTLA-4 on T cells and, at the same time, delivers a cancer antigen-targeting CAR, thereby simultaneously achieving enhanced therapeutic efficacy. For this purpose, the group I intron ribozyme from *Tetrahymena thermophila* was used to induce a trans-splicing reaction to CTLA-4 for its inhibition, and the expression of CAR was allowed to occur by gene replacement in order for T cells to have a targeting function for a specific cancer antigen. As a result, it was found that such an approach inhibits CTLA-4 on T cells which has been an obstacle in conventional anti-cancer therapies and, at the same time, enables an autoimmune-based anti-cancer therapy using a T cell which expresses CAR, thereby exhibiting effective anti-cancer effects in which both anti-cancer specificity and efficiency are enhanced. Thereby, the present invention has been completed.

Technical Solution

An object of the present invention is to provide a recombinant vector, characterized by including a cytotoxic T-lymphocyte-associated protein-4 (CTLA-4)-targeting trans-splicing ribozyme expression cassette for delivery of chimeric antigen receptor, wherein the expression cassette includes: (i) a CTLA-4-targeting trans-splicing ribozyme; and (ii) a polynucleotide encoding a chimeric antigen receptor connected to the 3' exon of the ribozyme.

Another object of the present invention is to provide a transformed cell into which the recombinant vector is introduced.

Still another object of the present invention is to provide a ribozyme expressed from the recombinant vector.

Still further object of the present invention is to provide a pharmaceutical composition for preventing or treating cancers, including, as an effective ingredient, the recombinant vector or the ribozyme.

Still further object of the present invention is to provide a method for treating cancers, including administering, to an individual in need thereof, a pharmaceutically effective amount of the recombinant vector or the ribozyme.

Advantageous Effects

The recombinant vector of the present invention and the ribozyme expressed therefrom become a gene-cell therapy which inhibits CTLA-4 on T cells which has been an obstacle in conventional anti-cancer therapies and, at the same time, enables anti-cancer treatment, thereby allowing more effective anti-cancer effects to be anticipated. Such a gene-cell therapy results in decreased toxicity in normal tissues and thus exhibits increased effects in both therapeutic efficacy and safety, which enables it to be widely utilized in the field of gene therapy in the future.

MODES OF THE INVENTION

Figure 1:
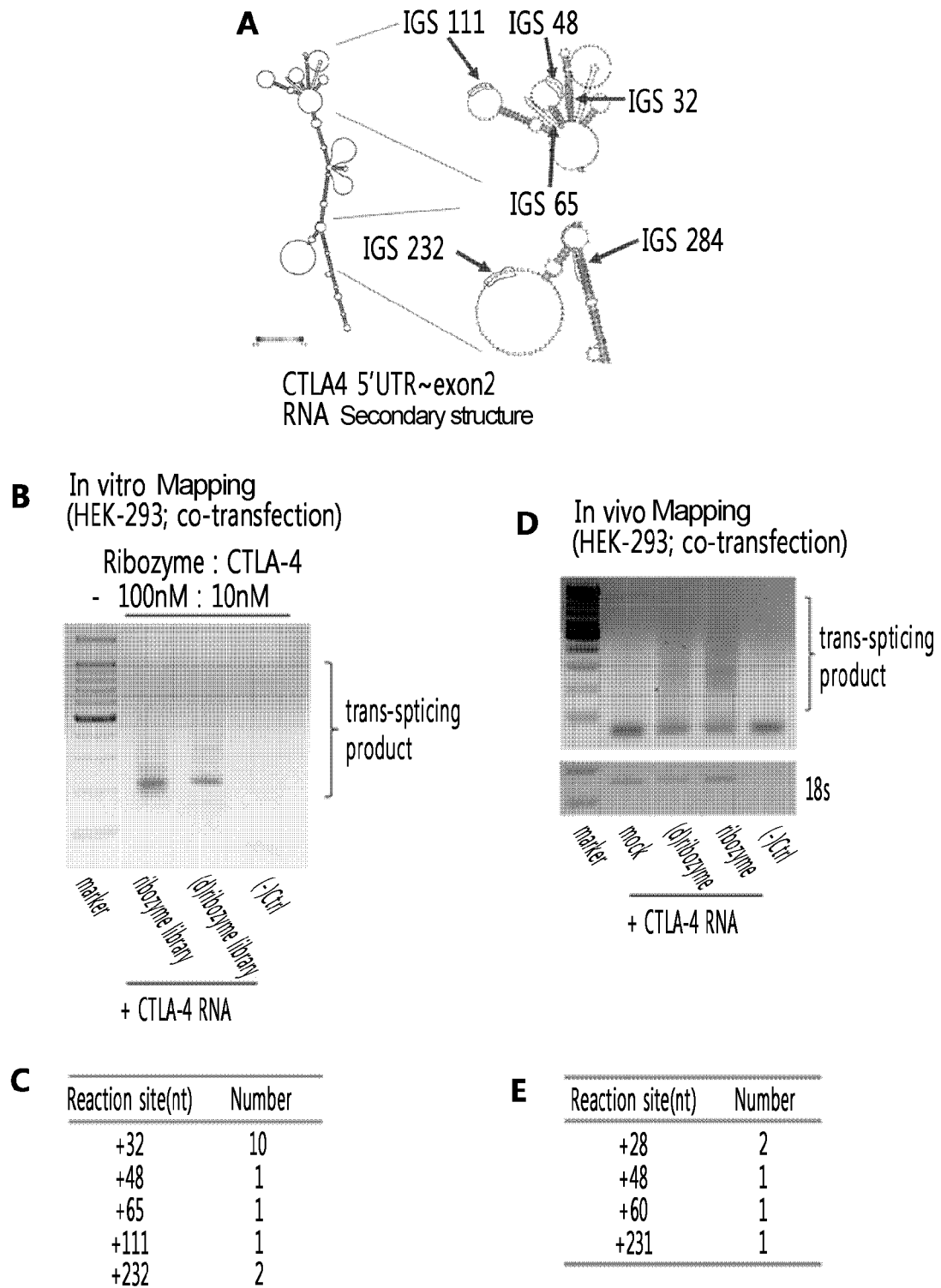
FIG. 1 illustrates the results of the in vitro and in vivo RNA mapping of the present invention which is conducted to find various recognition sites on CTLA-4 RNA. The major targeting sites by ribozyme are IGS32, IGS48, IGS65, IGS111 and IGS232. (A) shows the locations of IGS32, IGS48, IGS65, IGS111 and IGS232 which were identified as the major targeting sites by ribozyme on CTLA-4 RNA. (B) and (C) show the results of the in vitro RNA mapping. (D) and (E) show the results of the in vivo RNA mapping.

In order to achieve the above objects, in one aspect, the present invention provides a recombinant vector, characterized by including a cytotoxic T-lymphocyte-associated protein-4 (CTLA-4)-targeting trans-splicing ribozyme expression cassette for delivery of chimeric antigen receptor, in which the expression cassette includes: (i) a CTLA-4-targeting trans-splicing ribozyme; and (ii) a polynucleotide encoding a chimeric antigen receptor connected to the 3' exon of the ribozyme.

In one embodiment, the present invention provides the recombinant vector wherein the CTLA-4-targeting trans-splicing ribozyme targets one selected from the group consisting of the Internal Guide Sequences (IGSs) IGS32, IGS48, IGS111, and IGS232 on CTLA-4 RNA.

In the other embodiment, the present invention provides the recombinant vector, in which the CTLA-4-targeting trans-splicing ribozyme includes a nucleic acid sequence selected from the group consisting of SEQ ID NO: 1, SEQ ID NO: 2, SEQ ID NO: 3, and SEQ ID NO: 38.

In yet another embodiment, the present invention provides the recombinant vector, in which the chimeric antigen receptor recognizes a cancer cell-specific antigen.

In yet another embodiment, the present invention provides the recombinant vector, in which the cancer cell-specific antigen is selected from the group consisting of Epithelial glycoprotein 2 (EGP2), Epithelial glycoprotein 40 (EGP40), Tumor associated glycoprotein 72 (TAG72), Interleukin 13 receptor alpha-2 subunit (IL13Rα2), Carbonic anhydrase IX (CA IX), CD19, CD52, CD33, CD20, TSLPR, CD22, CD30, GD3, CD171, Anaplastic lymphoma kinase (ALK), CD47, EGFRvIII, Neural cell adhesion molecule (NCAM), Folate binding protein (FBP), Lewis-Y antigen (Le(Y)), Mucin 1 (MUC1), Prostate stem cell antigen (PSCA), Prostate-specific membrane antigen (PSMA), Fibroblast growth factor receptor 4 (FGFR4), Fetal acetylcholine receptor (FAR), Carcinoembryonic antigen (CEA), Human epidermal growth factor receptor 2 (HER2), Mesothelin, Hyaluronate receptor variant 6 (CD44v6), B7-H3, Glypican-3,5, ROR1, Survivin, folate receptor (FOLR1), Wilm's tumor antigen (WT1), CD70, and Vascular endothelial growth factor 2 (VEGFR2).

In yet another embodiment, the present invention provides the recombinant vector, in which the polynucleotide encoding a chimeric antigen receptor included in the recombinant vector includes the nucleic acid sequence of SEQ ID NO: 4.

In yet another embodiment, the present invention provides the recombinant vector, further including, at the 5' end of the ribozyme, (iii) a polynucleotide of an antisense sequence to 100 to 300 nucleotides of the base sequence downstream of the ribozyme's recognition site on CTLA-4.

In yet another embodiment, the present invention provides the recombinant vector, in which the antisense sequence includes the nucleic acid sequence of SEQ ID NO: 5 or 6.

In yet another embodiment, the present invention provides the recombinant vector characterized in that expression cassette includes a promoter selected from the group consisting of retrovirus LTR, cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter, and opsin promoter.

In further embodiment, the present invention provides a transformed cell into which the recombinant vector is introduced.

In still further embodiment, the present invention provides a ribozyme expressed from the recombinant vector.

In still further embodiment, the present invention provides a retrovirus expressing the ribozyme.

In still further embodiment, the present invention provides a T cell treated with the retrovirus.

In still further embodiment, the present invention provides a pharmaceutical composition for preventing or treating cancers, in which the pharmaceutical composition includes, as an effective ingredient, the recombinant vector or the ribozyme.

In one embodiment, a pharmaceutical composition for preventing or treating cancers is provided, in which the cancer is selected from the group consisting of lung cancer, pancreatic cancer, liver cancer, melanoma, bone cancer, breast cancer, colon cancer, leukemia, uterine cancer, lymphoma, and brain cancer.

In still further embodiment, the present invention provides a method for treating cancers, in which the method includes administering, to an individual in need thereof, the recombinant vector or the ribozyme.

Hereinafter, the present invention will be described in detail.

One aspect of the present invention relates to a recombinant vector, characterized by including a cytotoxic T-lymphocyte-associated protein-4 (CTLA-4)-targeting trans-splicing ribozyme expression cassette for delivery of chimeric antigen receptor, in which the expression cassette includes: (i) a CTLA-4-targeting trans-splicing ribozyme; and (ii) a polynucleotide encoding a chimeric antigen receptor connected to the 3' exon of the ribozyme. Specifically, the recombinant vector may one including a nucleic acid sequence selected from the group consisting of SEQ ID NO: 8, SEQ ID NO: 9, SEQ ID NO: 10, and SEQ ID NO: 11.

The recombinant vector is characterized in that it allows to develop an autoimmune-based anti-cancer therapeutic strategy which is excellent in terms of the therapeutic effect and such development is made based on the findings that the recombinant vector causes the expression of a chimeric antigen receptor to be induced such that the receptor targets CTLA-4 which interferes with the T cell-mediated immune response, thereby inhibiting the CTLA-4 related mechanism and, at the same time, allowing T cells to attack cells having a desired antigen without signal transduction process by antigen presenting cell (APC), thus achieving excellent anti-cancer effects.

As used herein, the term "vector" refers to an expression vector which allows a protein of interest to be expressed in an appropriate host cell, wherein the expression vector is a gene construct including essential regulatory elements operably linked to express a gene insert.

As used herein, the term "operably linked" refers to a state wherein a nucleic acid sequence coding for a protein of interest is functionally linked to an expression regulatory sequence for the nucleic acid such that general functions are exerted. For examples, a ribozyme-encoding sequence is operably linked to a promoter so that the expression of the ribozyme-encoding sequence is under the influence or control of this promoter. The two nucleic acid sequences (the ribozyme-encoding sequence and the promoter sequence at the 5' end thereof) are operably linked when the promoter function is induced to transcribe the ribozyme-encoding sequence, and the linkage between the two sequences does not induce a frame-shift mutation while not interfering with the ability of the regulatory sequence to dominate the expression of ribozyme. Operable linkage with a recombinant vector can be made using genetic recombination techniques well known in the art, and site-specific DNA cleavage and ligation can be achieved using enzymes generally known in the art.

The vector of the present invention may include a signal sequence or a leader sequence for membrane targeting or secretion in addition to an expression regulatory element such as a promoter, an operator, an initiation codon, a stop codon, a polyadenylation signal, and an enhancer, and may be variously constructed depending on its purpose. The promoter of the vector may be constitutive or inducible. Also, the expression vector includes a selectable marker for selecting a host cell including the vector, and includes an origin of replication in the case of a replicable expression vector. The vector may be self-replicating or integrated into host DNA. The vector may include a plasmid vector, a cosmid vector, or a viral vector, etc., and specifically, may be a viral vector. The viral vector includes, but not limited thereto, vectors derived from retroviruses such as human immunodeficiency virus (HIV), Murine leukemia virus (MLV), Avian sarcomdleukosis (ASLV), Spleen necrosis virus (SNV), Rous sarcoma virus (RSV), Mouse mammary tumor virus (MMTV), adenovirus, adeno-associated virus, herpes simplex virus and the like. More specifically, the recombinant vector of the present invention may be a recombinant adenoviral vector or an adeno-associated viral vector.

As used herein, the term "expression cassette" includes a promoter and a trans-splicing ribozyme gene of interest, and the trans-splicing ribozyme targets cytotoxic T-lymphocyte-associated protein-4 (CTLA-4), wherein the Internal Guide Sequence (IGS), which is a major targeting site by ribozyme on the CTLA-4 RNA sequence, may be particularly targeted. For example, the CTLA-4-targeting trans-splicing ribozyme of the present invention may target one selected from the group consisting of the internal guide sequences (IGSs), IGS32, IGS48, IGS111, and IGS232 on CTLA-4 RNA, and the ribozyme targeting the corresponding IGSs of CTLA-4 may include a nucleic acid sequence selected from the group consisting of SEQ ID NO: 1, SEQ ID NO: 2, SEQ ID NO: 3, and SEQ ID NO: 38.

Figure 2:
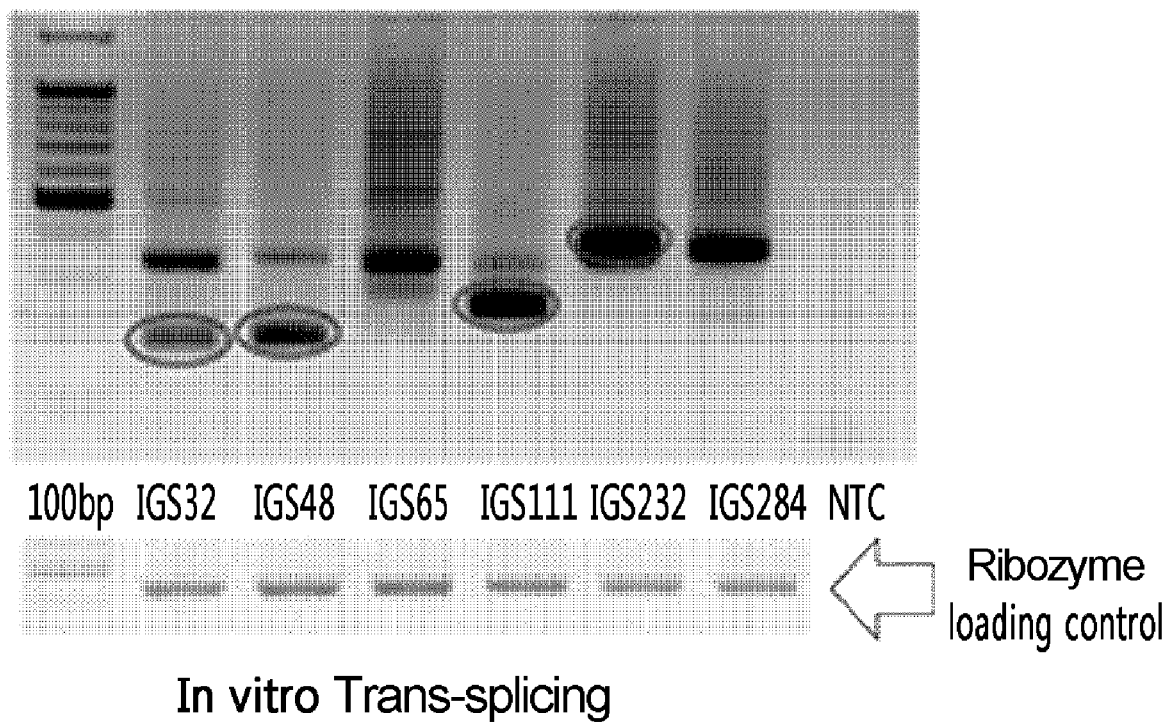
FIG. 2 illustrates a diagram which confirms that when the respective ribozymes for recognition sites (IGS48, IGS111 and IGS232) were constructed and used to perform in vitro trans-splicing, superior targeting has occurred in IGS32, IGS48, IGS111 and IGS232.

In a specific embodiment, in order to construct a ribozyme capable of effectively acting on CTLA-4 RNA, the present inventors initially performed in vitro and in vivo mapping to seek ribozyme internal guide sequences (Ribozyme IGSs) capable of recognizing, specifically and effectively, a specific sequence of CTLA-4 RNA. As a result of performing the in vitro and in vivo mapping, various trans-splicing products could be identified and sequenced to find various recognition sites. The thus identified major targeting sites by ribozyme were IGS32, IGS48, IGS111, and IGS232 (FIG. 1). In particular, the site identified as a common recognition site in both in vitro and in vivo mapping was IGS48. The respective ribozymes (IGS32: SEQ ID NO: 38; IGS48: SEQ ID NO: 1; IGS111: SEQ ID NO: 2; and IGS232: SEQ ID NO: 3) for the above identified recognition sites were constructed, and in vitro trans-splicing using some ribozymes confirmed that targeting occurred well in IGS32, IGS48, IGS111, and IGS232 (FIG. 2).

As used herein, the term "promoter" refers to a part of DNA which is involved in the binding of RNA polymerase to enable initiation of transcription. In general, it is located on the same strand as and adjacently upstream of the target gene, and is a site to which RNA polymerase or a protein introducing RNA polymerase, so-called transcription factor, is bound; and it can play a role of directing the enzyme or protein to be located at the correct transcription initiation site. That is, it is located at the 5' region of the gene to be transcribed on the sense strand and has a specific sequence allowing to direct RNA polymerase to bind to the correct site directly or through a transcription factor, thereby initiating mRNA synthesis for the target gene. In order to increase the expression of a gene, a universal promoter may be used, but not limited thereto, such as a promoter selected from the group consisting of retroviral LTR, cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter, and opsin promoter.

As used herein, the term "ribozyme" refers to a molecule composed of an RNA molecule acting like an enzyme or a protein including the RNA molecule, and is also called RNA enzyme or catalytic RNA. It has been found that ribozyme is a RNA molecule having a definite tertiary structure, performs a chemical reaction, and has a catalytic or self-catalytic property; and some ribozymes cleave themselves or other RNA molecules to inhibit the activity while other ribozymes catalyze the aminotransferase activity of ribosome. These ribozymes may include hammerhead ribozyme, VS ribozyme, hairpin ribozyme, Group I intron, Group II intron, and the like. In the present invention, a ribozyme may inhibit the activity of a cancer-specific gene through trans-splicing reaction, thereby exhibiting selective anti-cancer effects, while also being expressed in a form conjugated with a cancer therapeutic gene, thereby activating the cancer therapeutic gene. Therefore, any form of ribozyme may be used as long as it shows an activity capable of inactivating a cancer-specific gene and activating a cancer therapeutic gene. Specifically, the ribozyme may include the nucleic acid sequence of SEQ ID NO: 1, SEQ ID NO: 2, or SEQ ID NO: 3.

As used herein, the term "trans-splicing" refers to linking RNAs from different genes. Specifically, CTLA-4-targeting trans-splicing group I ribozyme may be used, which is proven to have the ability to recognize and trans-splice T cell-specific CTLA-4 mRNA.

On the other hand, the present inventors have devised, together with the ribozyme, a recombinant retrovirus capable of expressing a gene of interest. That is, the recombinant retrovirus may function to insert a gene of interest, which is included in an expression cassette for the gene of interest and linked to a ribozyme, into a T cell-specific gene transcript through a T cell-specific trans-splicing ribozyme.

As used herein, the term "gene of interest" refers to a gene whose expression is induced, via the ribozyme, by being linked to the mRNA of a specific target cancer-specific gene in a cell. In the present invention, it may be a therapeutic gene or reporter gene, but not limited thereto.

Furthermore, the gene of interest included in the expression cassette may be any gene that is intended to be expressed in place of CTLA-4 in T cells, and particularly, may be a chimeric antigen receptor (CAR) for the purpose of the present invention.

As used herein, the term "chimeric antigen receptor" may refer to a fusion protein for expression in T cells so that the fusion protein is capable of inducing activation of T cells through an antibody-antigen reaction by binding a desired antigen without involvement of APC which is naturally necessary for T cell activation, while attacking cells expressing the desired antigen. That is, it may be considered as a protein that, when expressed in T cells, binds to an antigen and induces T cell activation. It may also be a protein that recognizes an antigen specific to a cell to which an immune response is to be induced through the protein, and the cell to which an immune response is to be induced may refer to a cell that is present in a specific tissue or constitutes the tissue in which lesion has occurred.

For the purpose of the present invention, the chimeric antigen receptor may be one which recognizes a cancer cell-specific antigen, and the cancer cell-specific antigen may be one selected from the group consisting of Epithelial glycoprotein 2 (EGP2), Epithelial glycoprotein 40 (EGP40), Tumor associated glycoprotein 72 (TAG 72), Interleukin 13 receptor alpha-2 subunit (IL13Rα2), Carbonic anhydrase IX (CA IX), CD19, CD52, CD33, CD20, TSLPR, CD22, CD30, GD3, CD171, Anaplastic lymphoma kinase (ALK), CD47, EGFRvIII, Neural cell adhesion molecule (NCAM), Folate binding protein (FBP), Lewis-Y antigen (Le(Y)), Mucin 1 (MUC 1), Prostate stem cell antigen (PSCA), Prostate-specific membrane antigen (PSMA), Fibroblast growth factor receptor 4 (FGFR4), Fetal acetylcholine receptor (FAR), Carcinoembryonic antigen (CEA), Human epidermal growth factor receptor 2 (HER2), Mesothelin, Hyaluronate receptor variant 6 (CD44v6), B7-H3, Glypican-3,5, ROR1, Survivin, folate receptor (FOLR1), Wilm's tumor antigen (WT1), CD70, and Vascular endothelial growth factor 2 (VEGFR2), and particularly, may be TAG72. In the present invention, the chimeric antigen receptor may be encoded from a polynucleotide consisting of the nucleic acid sequence of SEQ ID NO: 4.

In a specific embodiment of the present invention, a ribozyme was cloned into a retroviral vector (pMT-CAR) including a Tag72 antigen-recognizing chimeric antigen receptor (CAR, SEQ ID NO: 4) from ViroMed to obtain pMT-Rib-CAR retroviral vector, and the pMT-Rib-CAR retroviral vector was mixed with an enveloped DNA and a gag-pol DNA, and then the mixture was spread on the cells to produce a retrovirus.

On the other hand, many attempts have been made to achieve effective anti-cancer therapy using the existing immune system. By causing a T cell to express CAR which recognizes specific antigens, a T cell directly attacking cancer cells has been developed without relying on APCs. However, it has been developed largely as a therapeutic for hematologic cancers. In the case of solid cancers where an environment suppressing immunological actions was created around cancer tissue, it is known that CAR exhibits low therapeutic effects.

In order to overcome this problem, attempts were made to maintain the activity of a T cell expressing CAR by inhibiting CLTA-4, which interferes with the activity of activated T cells, thereby achieving effective anti-cancer effects. Previous studies, which confirmed the anti-cancer effects by combined use of an anti-cancer drug and an antibody to CTLA-4, were reported. However, according to the previous studies, since such combined use induces an overall inhibition of CTLA-4, it results in low specificity and even adverse effects may be induced In the present invention, CTLA-4-targeting ribozyme is delivered to cytotoxic T cells, whereby the ribozyme inhibits CTLA-4 and, at the same time, allows to express CAR which recognizes a cancer antigen, thereby enhancing efficiency and reducing adverse effects. This ribozyme has been developed to express CAR by leaky expression and, when CTLA-4 is expressed in a state that T cells are activated, to inhibit CTLA-4 by trans-splicing of the ribozyme while at the same time enabling more increased expression of CAR.

Thus, when T cells recognize cancer cells and are activated thereby, this may maximize their anti-cancer effects by not only maintaining the activity of T cells but also expressing CAR for T cells to better recognize a cancer antigen. In other words, an effective anti-cancer gene-cell therapeutic agent has been developed, that overcomes the previous problems by inhibiting CTLA-4 which interferes with the existing anti-cancer therapies and, at the same time, inducing the expression of CAR, thereby enhancing both anti-cancer specificity and efficiency.

Particularly, when the ribozyme of the present invention is used, it allows the expression of CAR to occur continuously through leaky expression of CTLA-4, thereby achieving further improved anti-cancer effects.

On the other hand, the recombinant vector of the present invention may further include, at the 5' end of the ribozyme, (iii) a polynucleotide of an antisense sequence to the nucleotides downstream of the ribozyme's recognition site of CTLA-4. The antisense sequence may include 50 to 400 polynucleotides of the base sequence downstream of the ribozyme's recognition site of CTLA-4, and particularly, may include the nucleic acid sequence of SEQ ID NO: 5 or 6. In addition, the present invention may use an antisense sequence together with CMV, RSV promoters, etc. to achieve increased expression or specificity.

Figure 10:
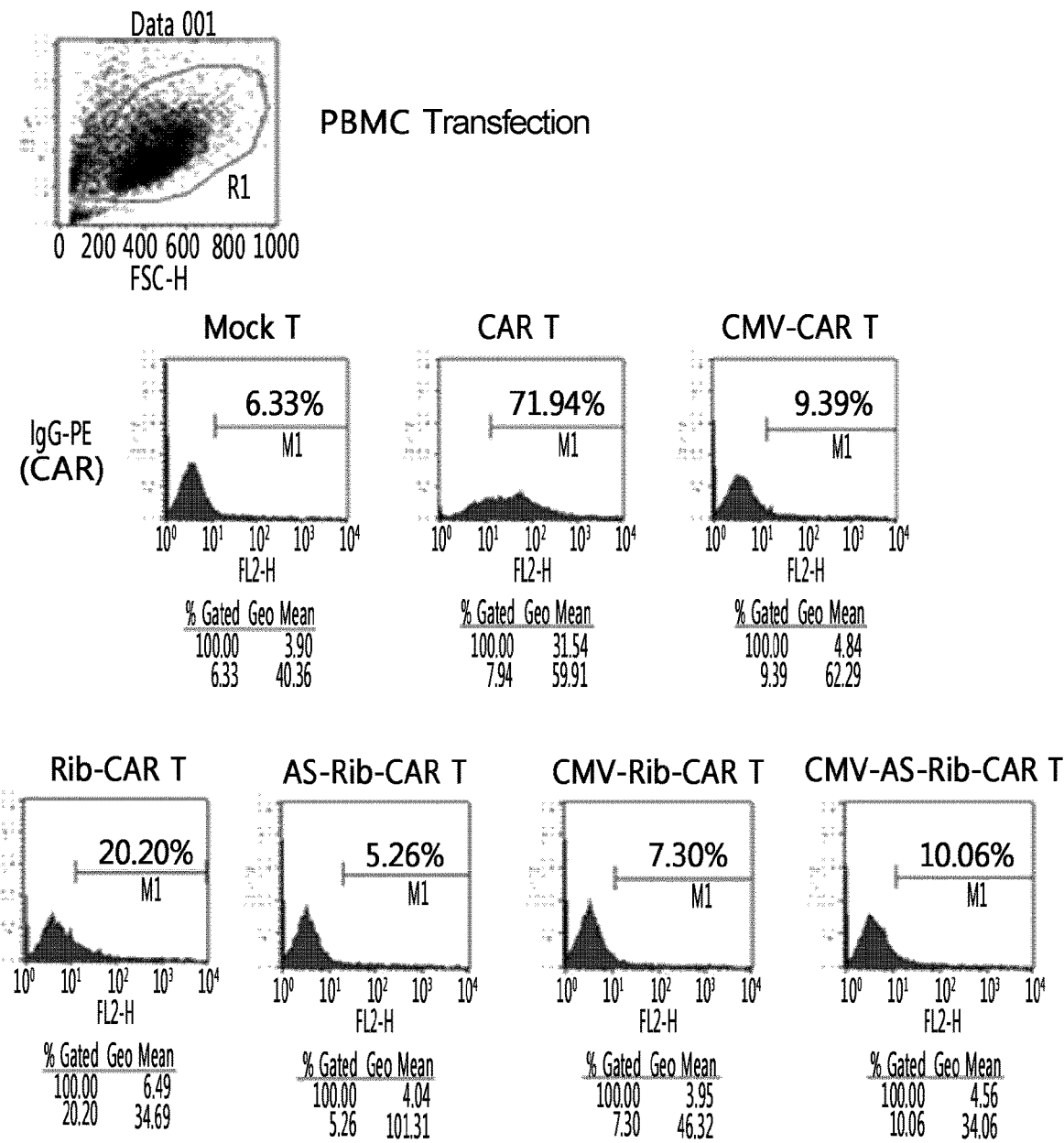
FIG. 10 is data obtained by confirming, through FACS, the expression of CAR in the T cell into which the ribozyme of the present invention was transferred. One (Mock T) into which a vacant retrovirus was transferred, was used as a negative control, and one (CAR T, CMV-CAR T) into which a CAR-expressing retrovirus was transferred, was used as a positive control. The percent CAR expression was confirmed by transferring Rib-CAR T, AS-Rib-CAR T, CMV-Rib-CAR T, and CMV-AS-Rib-CAR T which are representative among the ribozymes of the present invention.

In a specific embodiment of the present invention, it was found that the Ret-CMV-AS-CTLA-5 Rib48-CAR (CMV-AS-Rib-CAR T) construct having the structure of [CMV promoter-antisense 100 nt-CTLA-4 Rib48-CAR], in which an antisense sequence is additionally included, has superior intracellular expression effects compared to the Ret-CMV-CTLA-5 Rib48-CAR (CMV-Rib-CAR T) construct having the structure of [CMV promoter-CTLA-4 Rib 48-CAR] (FIG. 10).

In a still further embodiment, the present invention provides a transformed cell into which the recombinant vector is introduced.

As used herein, the term "introduction" refers to the entry of foreign DNA into cells through transfection or transduction. Transfection may be carried out using various methods well known in the art, including calcium phosphate-DNA co-precipitation, DEAE-dextran-mediated transfection, polybrene-mediated transfection, electroporation, microinjection, liposome fusion, lipofectamine, and protoplast fusion. Also, transduction may allow a gene to be delivered into cells using viruses or viral vector particles by means of infection.

As used herein, the term "transformed cell" refers to a host cell into which a polynucleotide of interest has been introduced. Transformation may be carried out by the above "introduction" method and may be done by selecting suitable standard techniques depending on the host cell as is known in the art.

In one embodiment of the present invention, a transformed cell into which a recombinant vector was introduced was prepared by injecting DNA into cells using recombinant vectors with PEI or using viruses as a vehicle. In addition, the transformed cell may be produced not by transient transduction but by a method of producing stable cells.

In a still further embodiment, the present invention provides a ribozyme expressed from the recombinant vector. Disclosures for recombinant vector and ribozyme in the present invention are as aforementioned.

In a still further embodiment, the present invention provides a retroviral vector expressing the ribozyme. Disclosures for ribozyme in the present invention are as described aforementioned.

In a still further embodiment, the present invention provides a T cell treated with the retrovirus. In the present invention, a T cell may be a primary T cell, particularly a human-derived primary T cell, but not limited thereto.

In the present invention, a T cell treated with the retrovirus may be the T cell which expresses the ribozyme, thereby resulting in decreased expression amount of CTLA-4 and CAR expression. Thus, the T cell may be activated by cells expressing an antigen which is recognized by CAR.

Figure 7:
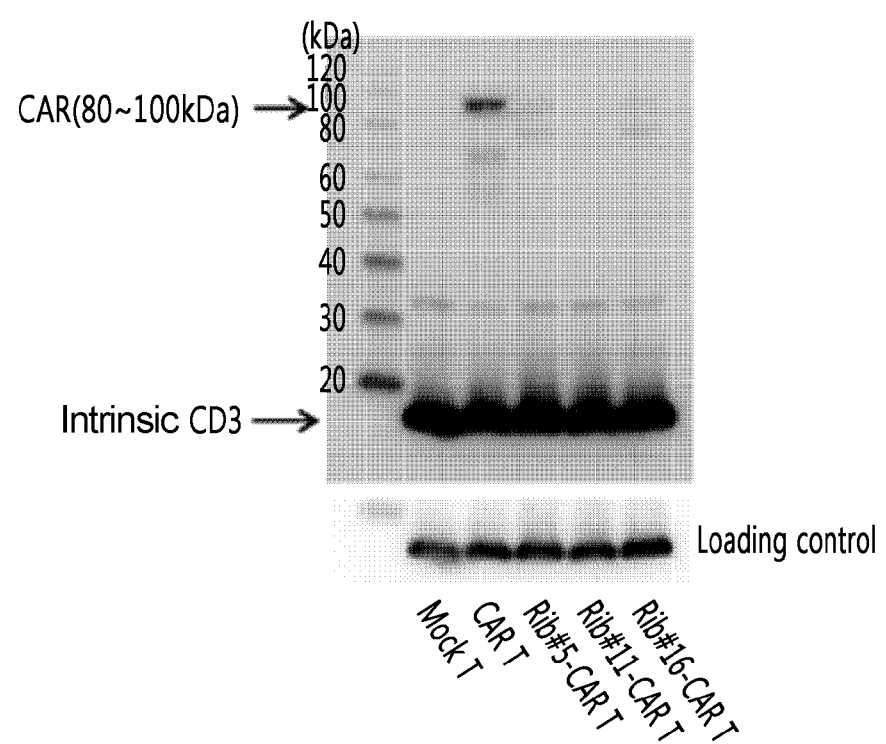
FIG. 7 shows the results of an experiment in which clones (Rib #5, Rib #11 and Rib #16) were obtained by constructing a retroviral vector with IGS48 ribozyme, and each cell was measured through Western blotting to confirm the expression level of CAR on the surface of the T cell into which these clones were transferred.
Figure 8:
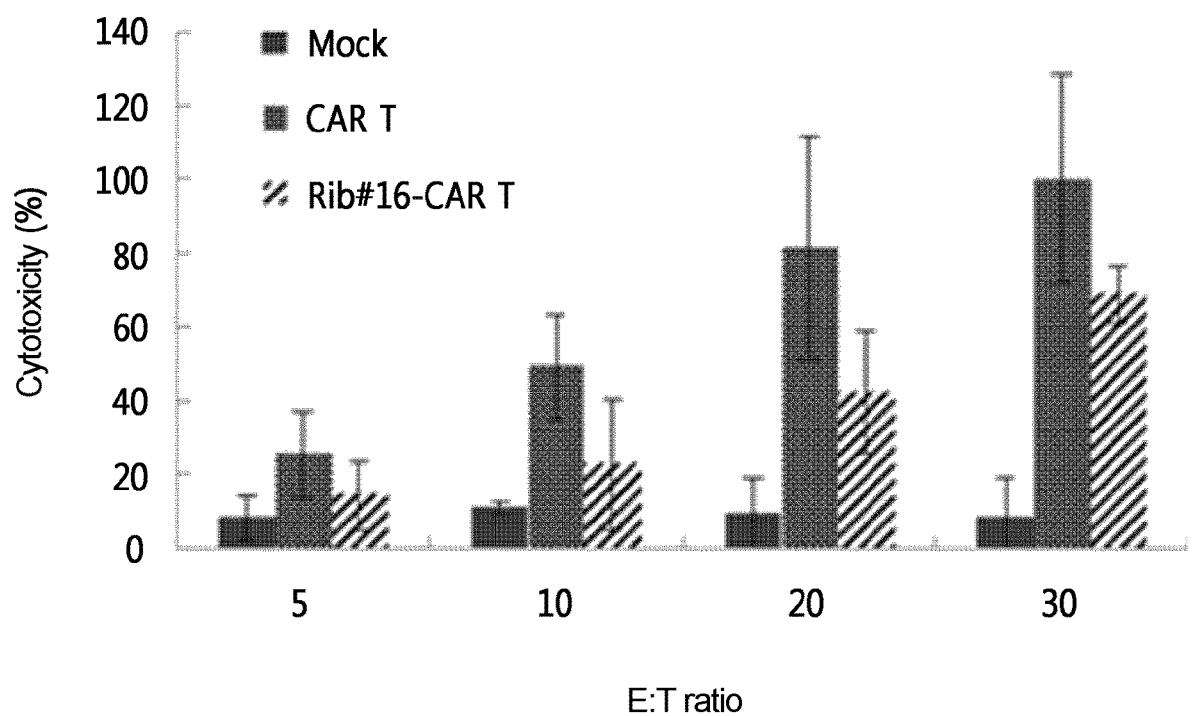
FIG. 8 shows the results of an experiment in which the retroviral vector constructed in the present invention, into which a ribozyme-CAR was cloned, was constructed as a virus (Ret-CTLA-4 Rib48-CAR, Rib #16-CAR T), this was transferred into primary T cells in order to confirm the induction of apoptosis (cytotoxicity) for cancer cells expressing Tag 72. In the experiment, T cell (CAR T), into which CAR-expressing retrovirus (Ret-CAR) without ribozyme was transferred, was used as a positive control. In the Figure, the E:T ratio is a ratio of target cell (LS174T):T cell, which, in turn, represents a ratio of 1:5, 1:10, 1:20, and 1:30.

As a specific embodiment of the present invention, the bottom of the culture dish was coated with retronectin and a retrovirus was allowed to adhere to the retronectin-coated culture dish. Primary T cells were placed on the culture dish to prepare retrovirus-treated T cells. Among the treated T cells, one in which the expression amount of CTLA-4 was decreased (FIG. 5), and one in which CAR was expressed (FIG. 6 and FIG. 7) were identified through semi-quantitative RT-PCR and Western blotting. However, the expression amount of CAR was significantly smaller than that of the CAR T cell into which simply a CAR expression cassette was injected without using ribozyme. In addition, the thus prepared T cell was applied to cancer cell line LS174T expressing Tag72, which is an antigen recognized by CAR, to confirm apoptosis-inducing effects. As a result, it was found that this T cell exhibited cytotoxicity about 5-fold that of a mock T cell, which corresponds to about 70% of that of the positive control (FIG. 8). This suggests that the activity of individual T cell was remarkably enhanced by additional inhibition of CTLA-4 or the like, considering that the expression amount of CAR was significantly smaller than that of CAR T which is a positive control.

In a still further embodiment, the present invention provides a pharmaceutical composition for preventing or treating cancers, including, as an effective ingredient, the recombinant vector, the transformed cell, the ribozyme, the retrovirus, the T cell, or a combination thereof.

As used herein, the term "cancer" refers to a state in which cells have abnormally hyper-proliferated due to the problems in the normal function of regulating the division, differentiation and death thereof and invaded the surrounding tissue and organ to form a mass and destroy or modify existing structures. Specifically, this cancer may be selected, but not limited thereto, from the group consisting of lung cancer, pancreatic cancer, liver cancer, melanoma, bone cancer, breast cancer, colon cancer, leukemia, uterine cancer, lymphoma, and brain cancer.

As used herein, the term "preventing" refers to all actions that inhibit cancer or delay the development of cancer by administering a composition including, as an effective ingredient, the recombinant vector, the transformed cell, the ribozyme, the retrovirus, the T cell, or a combination thereof.

As used herein, the term "treating" refers to all actions that alleviate or beneficially change cancer by administering a composition including, as an effective ingredient, the recombinant vector, the transformed cell, the ribozyme, the retrovirus, the T cell, or a combination thereof.

Figure 13:
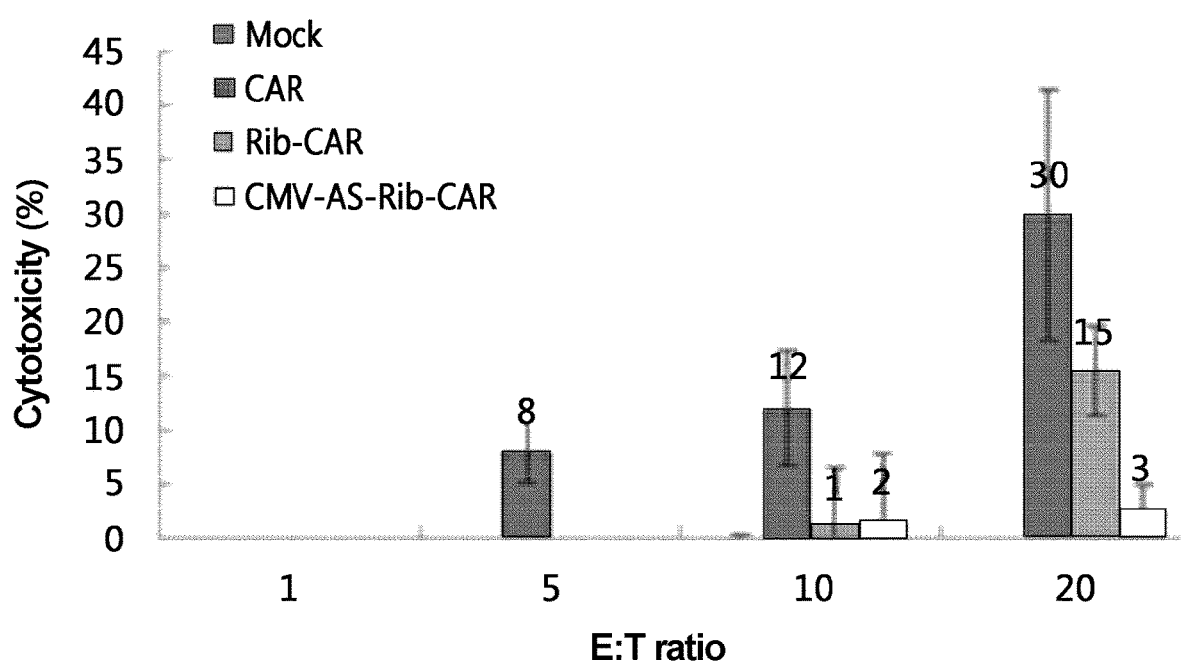
FIG. 13 is a diagram in which cytotoxic effects were confirmed by delivering each of Rib-CAR and CMV-AS-Rib-CAR, which are ribozymes of the present invention, via retrovirus to a primary T cell and applying the T cell to the cancer cell line LS174T expressing the Tag72 antigen. One (CAR) to which CAR T was delivered via retrovirus to a primary T cell, was used as a positive control, and one (Mock T) with which a vacant retrovirus was treated, was used as a negative control. In the Figure, the E:T ratio is a ratio of target cell (LS174T):T cell, which, in turn, represents a ratio of 1:1, 1:5, 1:10, and 1:20.
Figure 14:
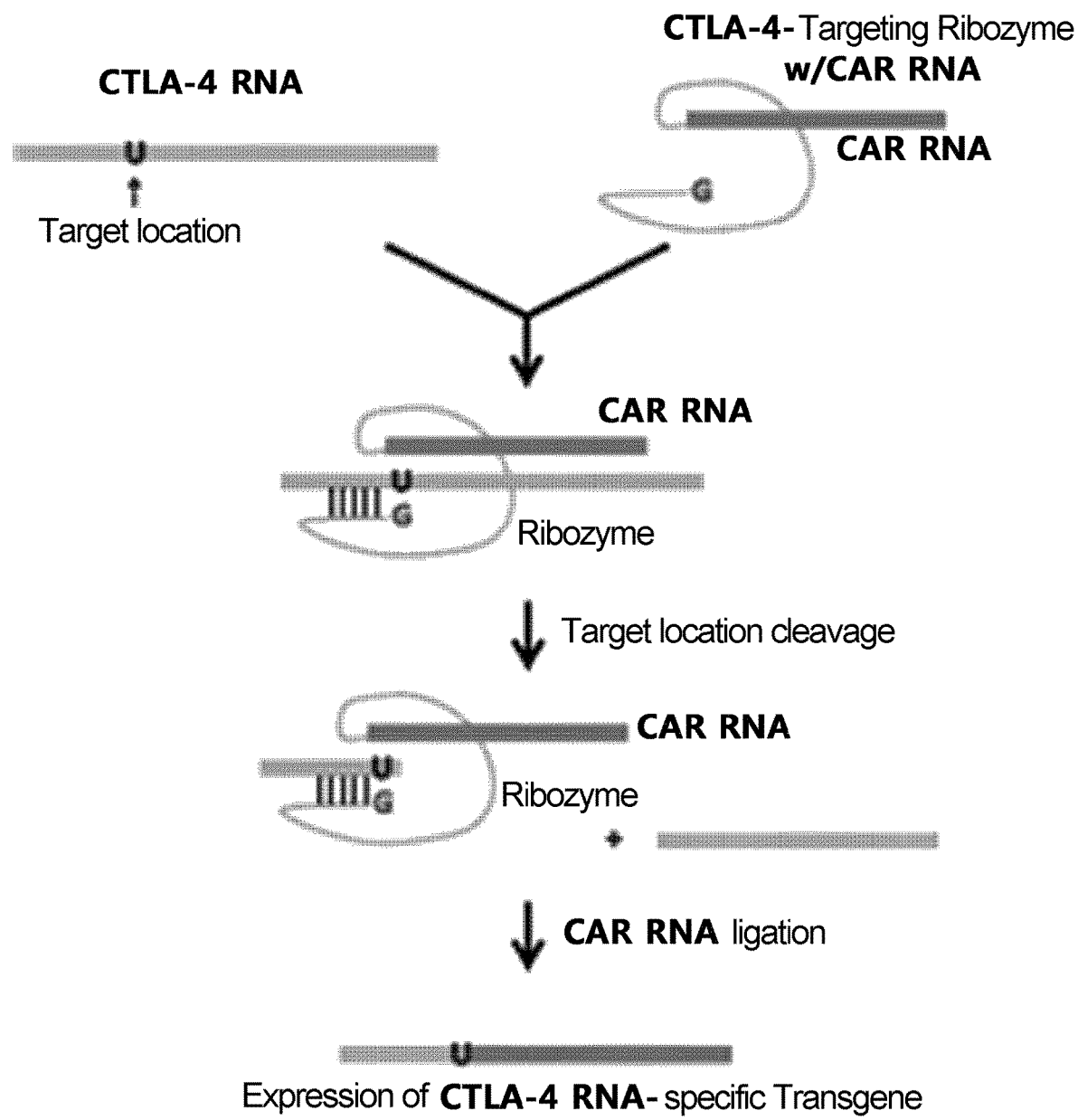
FIG. 14 is a schematic diagram for the trans-splicing scheme of the group I intron ribozyme used in the present invention.
Figure 15:
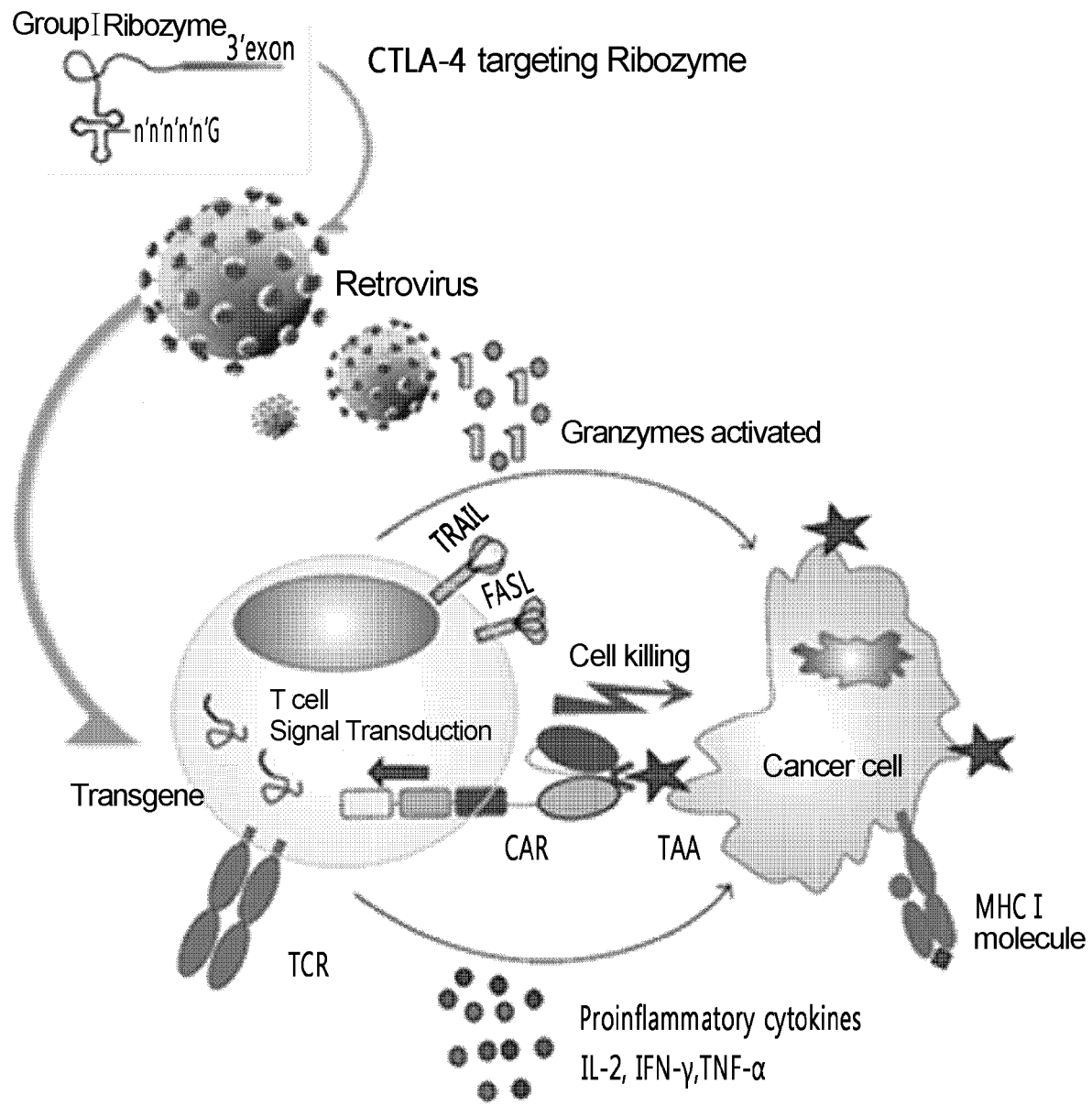
FIG. 15 is a schematic diagram showing the overall scheme on how the T cell of the present invention acts (a ribozyme-expressing retrovirus that targets CTLA-4 is transferred into T cells, and then CAR is expressed on the surface of T cells to attack tumor cells expressing Tag72).

As a specific embodiment of the present invention, the retroviral vector into which the ribozyme of the present invention was cloned, was transferred into primary T cells in order to confirm whether the retroviral vector exhibited cytotoxicity to the cell line LS174T expressing the Tag72 antigen. As a result, it was confirmed that Rib-CAR T of the present invention exhibited a killing ability in the order of 50 to 70% of the positive control CAR T. That is, it was confirmed that the ribozyme of the present invention has an actual cancer cell target-killing ability (FIG. 8 and FIG. 13).

The T cell expressing the ribozyme of the present invention not only has, against the cancer cells expressing a cancer-specific antigen, an excellent killing ability enough to reach 50 to 70% of a positive control, but also has an excellent effect which is a specific killing ability against cancer cells expressing the antigen.

In particular, the T cell expressing the ribozyme of the present invention can effectively maintain the anti-cancer effect of the T cell through a killing ability by decreasing the expression of CTLA-4 which is a T cell deactivation factor in vivo.

In addition, the pharmaceutical composition for preventing or treating cancers of the present invention may further include a pharmaceutically acceptable carrier, excipient or diluent.

Examples of a pharmaceutically acceptable carrier, excipient or diluent that may be used in the pharmaceutical composition of the present invention may include lactose, dextrose, sucrose, sorbitol, mannitol, xylitol, erythritol, maltitol, starch, acacia gum, alginate, gelatin, calcium phosphate, calcium silicate, calcium carbonate, cellulose, methyl cellulose, polyvinyl pyrrolidone, water, methyl hydroxybenzoate, propyl hydroxylbenzoate, talc, magnesium stearate, mineral oil, etc.

The pharmaceutical composition of the present invention may be formulated according to conventional methods in oral dosage forms, including powders, granules, tablets, capsules, suspensions, emulsions, syrup and aerosol, preparations for external application, suppositories, and sterile injectable solutions. The formulation may be done using commonly used diluents or excipients, such as fillers, extenders, binders, wetting agents, disintegrants, surfactants, etc. Examples of solid formulations for oral administration include tablets, pills, powders, granules, capsules and the like, and such solid formulations may be prepared by mixing at least one excipients, for example, starch, calcium carbonate, sucrose, lactose or gelatin. In addition to simple excipients, lubricants such as magnesium stearate or talc may also be used.

Liquid formulations for oral administration include suspensions, solutions, emulsions, and syrup, and may include various excipients, for example, wetting agents, flavoring agents, aromatics and preservatives, in addition to water and liquid paraffin which are frequently used simple diluents.

Formulations for parenteral administration include sterilized aqueous solutions, non-aqueous solutions, suspensions, emulsions, freeze-dried preparations, and suppositories. In non-aqueous solutions or suspensions, propylene glycol, polyethylene glycol, vegetable oils such as olive oil, injectable esters such as ethyl oleate, and the like may be used. As the base of the suppositories, witepsol, Macrogol, Tween 61, cacao butter, laurin fat, glycerogelatin and the like may be used.

In a still further embodiment, the present invention provides a method for treating cancers, including administering, to an individual in need thereof, a pharmaceutically effective amount of the recombinant vector, the transformed cell, the ribozyme, the retrovirus, the T cell, or a combination thereof.

As used herein, the term "pharmaceutically effective amount" refers to an amount sufficient to treat diseases, at a reasonable benefit/risk ratio applicable to any medical treatment. The effective dosage level may be determined depending on the subject's age and sex, the disease's type, the disease severity, the activity of the drug, sensitivity to the drug, the time of administration, the route of administration, excretion rate, the duration of treatment, factors including drugs used at the same time, and other factors known in the medical field. The recombinant vector, the transformed cell, the ribozyme, the retrovirus, the T cell, or a combination thereof according to the present invention may be administered individually or in combination with other therapeutic agents, and may be administered sequentially or simultaneously with conventional therapeutic agents. The recombinant vector, the transformed cell, the ribozyme, the retrovirus, the T cell, or a combination thereof according to the present invention may be administered in either a single dose or multiple doses. It is important to administer an amount which is the minimum amount that may exhibit the maximum effect without causing adverse effects, in consideration of all the above-described factors, and this amount can be easily determined by a person skilled in the art.

As used herein, the term "individual" is intended to encompass humans or animals such as horses, sheep, pigs, goats, camels, antelope, and dogs, having a cancer, symptoms of which may be ameliorated by administering the recombinant vector, the transformed cell, the ribozyme, the retrovirus, the T cell, or a combination thereof according to the present invention. Cancer may be effectively prevented and treated by administering, to an individual, the recombinant vector, the transformed cell, the ribozyme, the retrovirus, the T cell, or a combination thereof according to the present invention. The treatment method according to the present invention may be a method of treating an animal other than a human, but not limited thereto. That is, in the case of humans, considering that they have a cancer, symptoms of which may be ameliorated by administering the recombinant vector, the transformed cell, the ribozyme, the retrovirus, the T cell, or a combination thereof according to the present invention, the treatment method may be also sufficiently used in human therapy.

As used herein, the term "administering" refers to introducing a predetermined substance into an animal by any suitable method. The recombinant vector, the transformed cell, the ribozyme, the retrovirus, the T cell, or a combination thereof according to the present invention may be administered orally or parenterally by any general route, as long as it can reach a target tissue. In addition, the recombinant vector, the transformed cell, the ribozyme, the retrovirus, the T cell, or a combination thereof according to the present invention may be administered using any device capable of causing the active ingredient to be delivered to target cells.

The preferred dosage of the recombinant vector, the transformed cell, the ribozyme, the retrovirus, the T cell, or a combination thereof according to the present invention may vary depending on the patient's conditions and weight, the severity of disease, the type of formulation, the route and duration of administration, but may be selected appropriately by a person skilled in the art. However, for desired effects, the recombinant vector, the transformed cell, the ribozyme, the retrovirus, the T cell, or a combination thereof according to the present invention may be administered in a daily dosage of 1 to 10 mg/kg, and preferably 1 to 5 mg/kg. The daily dosage may be taken in a single dose, or may be divided into several doses.

The recombinant vector, the transformed cell, the ribozyme, the retrovirus, the T cell, or a combination thereof according to the present invention may be used alone or in combination with known anti-cancer drugs or with auxiliary therapeutic methods such as surgical therapy in order to enhance its anti-cancer effects. Chemotherapeutic agents that may be used together with administration of the recombinant vector, the transformed cell, the ribozyme, the retrovirus, the T cell, or a combination thereof according to the present invention may include, but not limited thereto, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, methotrexate, and the like. In addition, radiotherapies that may be used together with administration of the recombinant vector, the transformed cell, the ribozyme, the retrovirus, the T cell, or a combination thereof according to the present invention include, but not limited thereto, X-ray irradiation and γ-ray irradiation.

For a better understanding, the present invention will be described in detail with reference to preferred examples. It is to be understood, however, that these examples are for illustrative purposes only and are not intended to limit the scope of the present invention.

Example 1. Construction of Ribozyme 1-1. In Vitro Mapping of CTLA-4 RNA

In order to construct a ribozyme capable of effectively acting on CTLA-4 RNA, in vitro mapping was initially performed to seek ribozyme internal guide sequences (Ribozyme IGSs) capable of recognizing, specifically and effectively, a specific sequence of CTLA-4 RNA.

Specifically, for trans-splicing reaction, ribozyme library RNA, in which IGSs are randomized, and CTLA-4 RNA were reacted at 100 nM:10 nM in an absolute amount, respectively. Prior to the reaction, the substrate CTLA-4 RNA (2× reaction buffer, substrate RNA, 0.2 mM dGTP, DEPC-$H_2O$) was previously preheated at 37° C. for 5 minutes, and ribozyme RNA (2× reaction buffer (Ribozyme RNA, DEPC-$H_2O$) was allowed to stand at 50° C. for 5 minutes and then to stand at 37° C. for 2 minutes to induce correct tertiary structure formation. The two reactants (CTLA-4 RNA solution and ribozyme RNA solution) were mixed well and reacted at 37° C. for 3 hours.

10 μl of the reaction mixture was mixed well with primer (RY-RT), which is attached to the 3' portion of the ribozyme library RNA, and purified total RNA, and reacted at 65° C. for 5 minutes and placed on ice for 10 minutes. To this were added 5×RT buffer, 10 mM dNTP mix (Beams bio), 1 U MMLV Reverse transcriptase (abm), 16 U RNase inhibitor (Enzynomics) and DEPC $dH_2O$, which were prepared to total 50 μl, and reacted at 42° C. for 1 hour. After the reaction for 1 hour, the mixture was allowed to react at 95° C. for 5 minutes to completely inactivate the activity of MMLV-RT and placed at 4° C. Then, 10× taq polymerase buffer, 10 mM dNTP mix (beams bio) and 1 U taq polymerase (Solis BioDyne) were added together with 5' primer (CTLA-4 5' UTR XhoI) and 3' primer (RT-TS), adjusted to 20 μl using distilled water, and then PCR was performed under the conditions of [95° C., 5 min (95° C., 30 sec 58° C., 30 sec 72° C., 30 sec)×40 cycles 72° C., 5 min]. The resulting product was loaded on a 2% TAE agarose gel, allowed for all bands to be eluted, cloned into a T-blunt vector (Solgent) for sequencing, and then sequenced.

1-2. In Vivo Mapping of CTLA-4 RNA

In the case of in vivo mapping, 5 μg of CTLA-4 RNA (substrate, 5'UTR to exon 2 region) and 4 μg of ribozyme library RNA were co-transfected into 293 cells with DMRIE-C Reagent (Invitrogen), and then after 24 hours, total RNA was purified. Then, the purified RNA was mixed well with primer (RY-RT), which is attached to the 3' portion of the ribozyme library RNA, and reacted at 65° C. for 5 minutes and placed on ice for 10 minutes. To this were added 5λ RT buffer, 10 mM dNTP mix (Beams bio), 1 U MMLV Reverse transcriptase (abm), 16 U RNase inhibitor (Enzynomics) and DEPC $dH_2O$, which were prepared to total 50 μl, and reacted at 42° C. for 1 hour. After the reaction for 1 hour, the mixture was allowed to react at 95° C. for 5 minutes to completely inactivate the activity of MMLV-RT and placed at 4° C. Then, 10× taq polymerase buffer, 10 mM dNTP mix (beams bio) and 1 U taq polymerase (Solis BioDyne) were added together with 5' primer (CTLA-4 5' UTR XhoI) and 3' primer (RT-TS), adjusted to 20 μl using distilled water, and then PCR was performed under the conditions of [95° C., 5 min→(95° C., 30 sec→58° C., 30 sec→72° C., 30 sec)×40 cycles→72° C., 5 min]. The resulting product was loaded on a 2% TAE agarose gel, allowed for all bands to be eluted, cloned into a T-blunt vector (Solgent) for sequencing, and then sequenced.

1-3. Mapping of Sites on CTLA-4 RNA Targeted by Ribozyme

As a result of in vitro and in vivo RNA mapping performed in Examples 1-1 and 1-2, RT-PCR allowed to identify trans-splicing products, which were produced by trans-splicing, by recognizing various sites, and the products were sequenced to identify various recognition sites. The thus identified major targeting sites by ribozyme were IGS32, IGS48, IGS111, and IGS232 (FIG. 1). In particular, the site identified as a common recognition site in both in vitro and in vivo mapping was IGS48.

The respective ribozymes (IGS32: SEQ ID NO: 38; IGS48: SEQ ID NO: 1; IGS111: SEQ ID NO: 2; and IGS232: SEQ ID NO: 3) for the above identified recognition sites were constructed, and in vitro trans-splicing using the ribozymes confirmed that targeting occurred well in IGS32, IGS48, IGS111, and IGS232 (FIG. 2).

1-4. Construction of Ribozyme with Increased Specificity

PCR was performed for IGS of ribozyme using 5' primer (IGS48P1P10 StuI) and 3' primer (RY-RT)/5' primer (IGS111P1P10 StuI) and 3' primer (RY-RT)/5' primer (IGS232P1P10 StuI) and 3' primer (RY-RT), which include P1 and P10, and then ligation was performed using T4 ligase (doctor protein) at 16° C. for 4 hours together with SV40 promoter vector which was digested with StuI and ScaI.

Then, the vector into which the ribozyme was cloned, was double-digested with ScaI and XhoI, and then to this was ligated the firefly luciferase gene which was obtained by PCR with each of 5' primers (5' F.luci ScaI P10 IGS48, 5' F.luci ScaI P10 IGS111, 5' F.luci ScaI P10 IGS232) and 3' primer (3' F.luci end XhoI). Here, in the case of ribozyme recognizing IGS232, since it was ligated behind CTLA-4, the reading frame was adjusted for the transgene protein to be correctly expressed.

Subsequently, cloning was performed to transfer what was cloned into SV40 promoter vector to pcDNA3.1 (+) vector. First, pcDNA3.1 (+) vector was prepared by double-digestion with HindIII and XhoI, and PCR was performed for F. luciferase gene from ribozyme with each of 5' primers (IGS48 P1P10 HindIII, IGS111P1P10 HindIII and IGS232 P1P10 HindIII) and 3' primer (3' F.luci end XhoI), and then they were ligated together. Sequence analysis confirmed that ribozyme having P1 and P10 structures was cloned into pcDNA3.1 (+) vector having a CMV promoter, with firefly luciferase, which is a reporter gene, cloned following the ribozyme.

On the other hand, an additional ribozyme, which is the ribozyme as prepared above further including an antisense sequence to CTLA-4, was prepared to enhance the specificity and/or efficiency of ribozyme activity on CTLA-4. An attempt was made to clone, to the 5' of the ribozyme having IGS48, as an antisense 100 nt (SEQ ID NO: 5) or 300 nt (SEQ ID NO: 6) downstream of the ribozyme's recognition site on CTLA-4. PCR was performed for the antisenses 100 nt and 300 nt using 5' primer (IGS48 AS100 kit F) and 3' primer (IGS48 AS kit R)/5' primer (IGS48 AS300 kit F) and 3' primer (IGS48 AS kit R), respectively, in PcDNA3.1(+)-CTLA-4 plasmid, thereby eluting DNA. After digestion of pcDNA3.1(+)-ribozyme-F.luciferase plasmid with HindIII, 100 μg each of vector and insert were mixed with 5× infusion mix (Clontech) and reacted at 65° C. for 15 minutes. Then, the mixture was cooled on ice for a while, transformed into DH5a *E. coli*, screened for the cloned vectors, and identified by sequencing.

Example 2. Activity Comparison of Ribozymes with Different Recognition Sites

Experiments were performed to confirm the intracellular function and efficiency of each ribozyme which recognizes the specific sites of CTLA-4 identified by mapping.

HEK-293 cells were seeded in a 35 mm dish at $3 \times 10^5$ cells. After 24 hours, two tubes were prepared, one tube in which 1 μg of DNA was added to 500 μl of serum-free media, and the other tube to which 500 μl of serum-free medium and 3 μl of DMRIE-C (Invitrogen) were added. The two tubes were mixed well to allow DNA to form complexes in the form of a liposome which is capable of entering cells well, followed by incubation at room temperature for 30 minutes. For RNA, 1000 μl of serum-free medium and 3 μl of DMRIE-C (Invitrogen) were mixed and 5 μg of RNA was rapidly mixed immediately before transformation. After incubation for 4 h in a 5% $CO_2$ incubator, the medium was replaced with MEM media (Hyclone) including 10% FBS and 1% Penicillin/Streptomycin.

To 100 μL of 150 mM NaCl were added pcDNA3.1(+)-Ribozyme-F.luciferase (0.5 μg) and target DNA (2.5 μg), and together with them added 200 ng of *Renilla* luciferase DNA to correct the transformation efficiency. PEI (6 μg) was mixed with 100 μl of 150 mM NaCl in another tube, incubated at room temperature for 5 minutes, aliquoted at 100 μl to each tube and mixed, wherein each tube includes a mixture of ribozyme and target DNA, followed by incubation at room temperature for 20 minutes, and then 200 μl each of the mixture of DNA and PEI was slowly added to HEK-293. After 24 hours, all media were removed from the transformed cells, washed with 1×PBS, and lysed for 15 minutes at room temperature by adding 200 μl of 1× passive lysis buffer. The cell lysate was transferred to a 1.5 ml tube, centrifuged, and the supernatant except for cell debris was transferred to a new tube to obtain total protein. After transferring 20 μl of cell lysate into a 1.5 ml tube, each 100 μl of LARII (Luciferase assay reagent II, Promega) was added and mixed, and then read with Luminometer (TD+ 20/20). Then, each 100 μl of Stop & Glo reagent mix (Stop & Glo 20 μl+buffer 1 ml, promega) was added and mixed in the same manner, and also read with Luminometer. Here, mixing time and number for the two reagents were made same, and the sensitivity level was set between 20% and 60% depending on each cell condition.

As described above, the 3' exon is labeled with the firefly luciferase gene, which is a reporter gene, to confirm the target-specific efficiency of ribozyme and the respective ribozymes (SEQ ID NOS: 13, 16, and 17) were constructed for IGS48 which is the 5' UTR and located in the loop region and for IGS111 and IGS232 which are the ORF and loop region. Here, in addition to IGS, P1 and P10 helix were added to improve specificity and efficiency.

Figure 3:
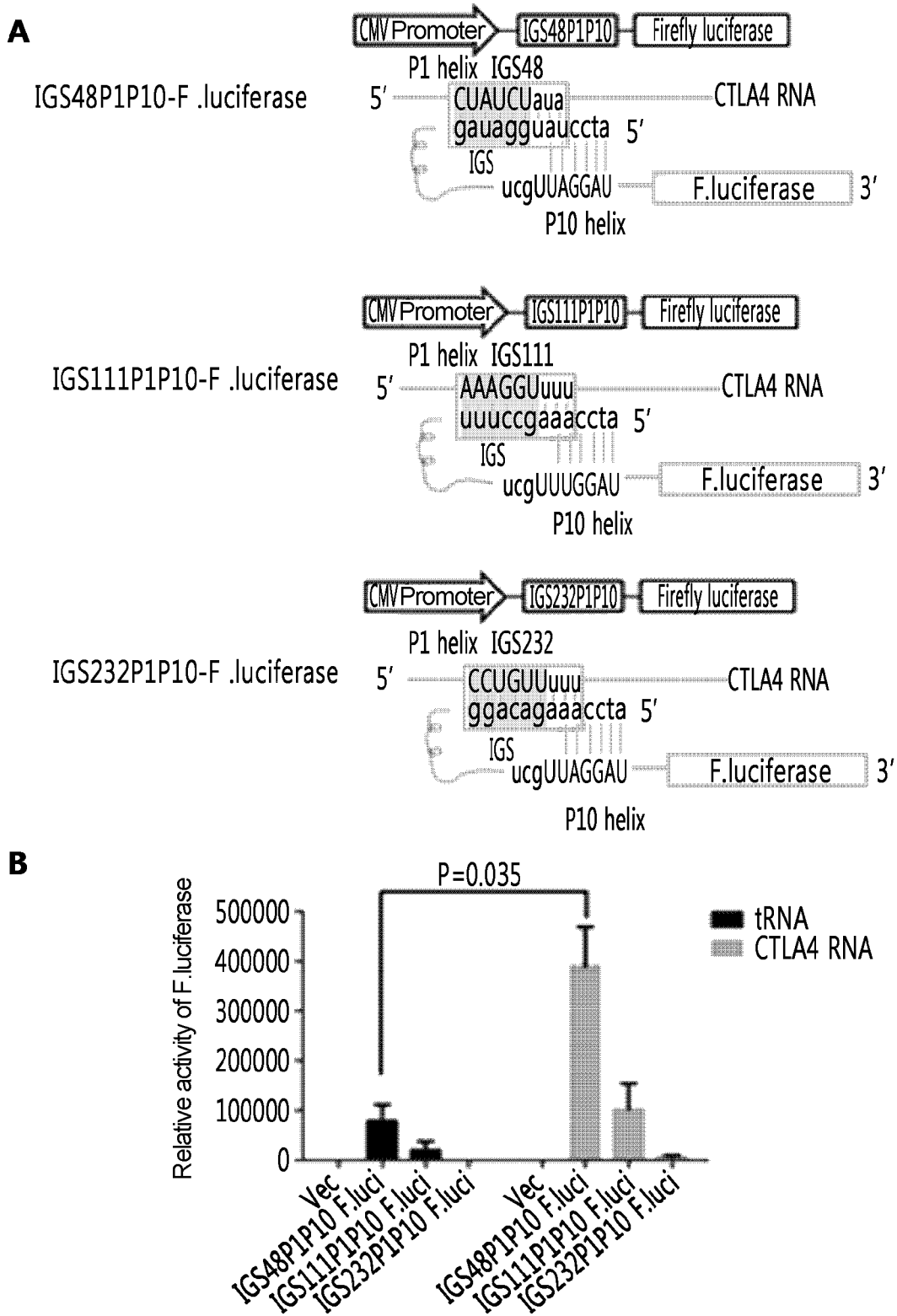
FIG. 3 shows the results of an experiment in which the 3' exon is labeled with the firefly luciferase gene, which is a reporter gene, to confirm the target-specific efficiency of ribozyme and the respective ribozymes were constructed for IGS48 which is the 5' UTR and located in the loop region and for IGS111 and IGS232 which are the ORF and loop region. Here, in addition to IGS, P1 and P10 helix were added to improve specificity and efficiency. (A) is a schematic diagram showing the ribozyme expression cassettes prepared as above and their action mechanism. (B) shows that the following was confirmed by measurement of effects of the ribozymes prepared as above through the luciferase activity: the efficiency of ribozymes was increased by trans-splicing when the target RNA was present, and the highest efficiency was observed in the ribozyme having IGS48 (IGS48P1P10 F.luci).

As a result, it was confirmed that the efficiency of ribozyme was increased by trans-splicing in the presence of target RNA, and the highest efficiency was observed in ribozyme having IGS48 (IGS48P1P10 F.luci). In addition, it was confirmed that leaky expression occurs well in IGS48P1P10 ribozyme in the absence of target gene. That is, IGS48P1P10 ribozyme, which has the highest efficiency of ribozyme and permits leaky expression to occur well, was selected as a representative ribozyme of the present experiment and then the next experiment was conducted therewith (FIG. 3).

In addition to the above experiment, the 3' exon is labeled with the firefly luciferase gene, which is a reporter gene, to confirm the target-specific efficiency of ribozyme, and the activity of ribozyme was confirmed for the case in which only ribozyme is present without any antisense, and for the case in which ribozyme is present together with each of 100 nt and 300 nt of antisense to CTLA-4 (AS100-IGS48P1P10-F.luci-SEQ ID NO: 14 and AS300-IGS48P1P10-F.luci-SEQ ID NO: 15, respectively). Here, a vector (Vec) having only a CMV promoter was used as a negative control, and a vector (CF) having a CMV promoter and expressing F. luciferase was used as a positive control.

Figure 4:
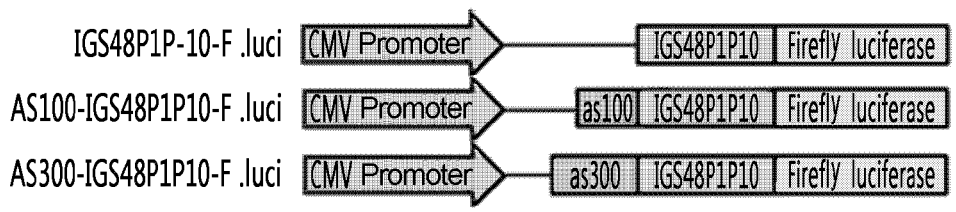
FIG. 4 shows the results of an experiment in which the 3' exon is labeled with the firefly luciferase gene, which is a reporter gene, to confirm the target-specific efficiency of ribozymes, and the activity of ribozymes is confirmed without any antisense and in the presence of 100 nt of antisense and 300 nt of antisense for CTLA-4 (AS100-IGS48P1P10-F.luci and AS300-IGS48P1P10-F.luci, respectively).
Figure 4:
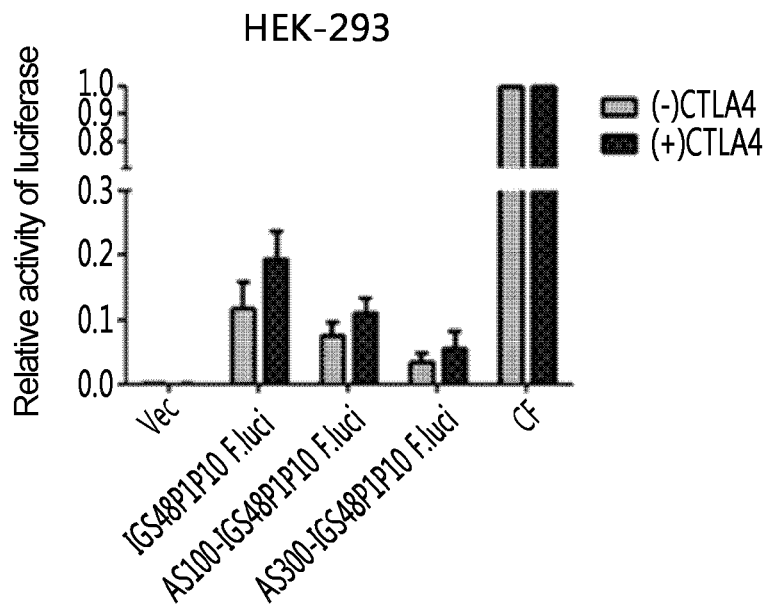
Figure 4:
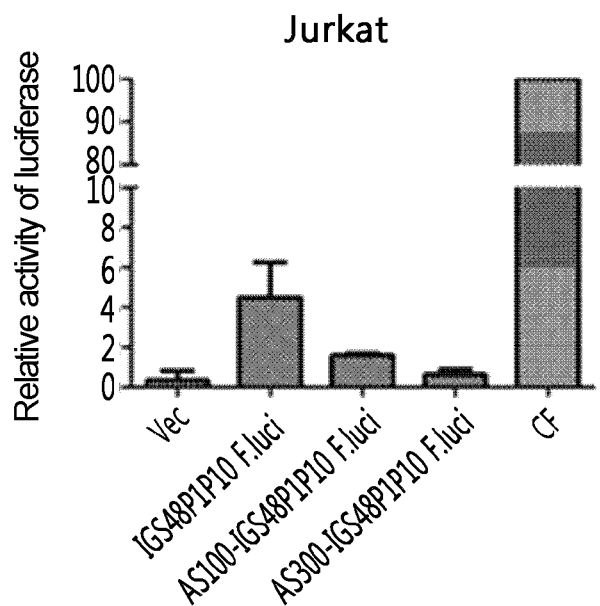

As a result, it could be confirmed that the activity was increased in all cases in the presence of target RNA, and ribozyme having no antisense added showed the highest activity in vitro. In addition, ribozyme activity could be confirmed for all cases also in Jurkat cell line expressing CTLA-4 intrinsically, and it was confirmed that IGS48P1P10 ribozyme having no antisense showed the highest activity (FIG. 4).

On the other hand, in the present invention, AS100-IGS48P1P10-F.luci and AS300-IGS48P1P10-F.luci were introduced into pcDNA3.1 (+) (CMV promoter-including vector) to confirm their activity.

Example 3: Construction and Production of Ribozyme-Expressing Retroviral Vector 3-1. Construction of Ribozyme-Expressing Retroviral Vector A ribozyme was cloned into a retroviral vector (pMT-CAR) including a Tag72 antigen-recognizing chimeric antigen receptor (CAR, SEQ ID NO: 4) from ViroMed. In particular, as confirmed in Example 2 above, a retroviral vector was constructed by using IGS48 ribozyme, which has the highest efficiency of ribozyme and permits leaky expression to occur well, to confirm the activity of the ribozyme.

Specifically, PCR was performed using primer (IGS48 BamHI F, IGS48Rib BamHI R) from the PcDNA3.1(+)-IGS48 ribozyme-F.luciferase plasmid, and then DNA was eluted to obtain an insert. pMT-CAR vector was prepared by digestion with BamHI to allow CAR to be expressed with 3' exon of IGS48 ribozyme. The vector and insert were subjected to ligation reaction at 16° C. Clones were screened with BamHI and sequenced to obtain three clones of #5, #11, and #16 (pMT-Rib-CAR).

3-2. Production of Retrovirus

Twenty-four hours before, preparation was made by seeding 293T cells on a 60 mm cell culture dish at 1×10⁶ cells each. To a 1.5-ml tube, were added and mixed 600 μl of serum-free media and 18 μl of 293T transfection reagent (Mirus), and incubated at room temperature for 5 minutes. Then, each of the previously constructed pMT-Rib-CAR retroviral vectors was mixed with an envelope DNA and a gag-pol DNA at a ratio (2.4 ug:1.2 ug:2.4 ug) and placed in a tube, reacted at room temperature for 30 minutes, and then slowly spread on the cells. After 4 hours, the cells were rinsed twice with 1×PBS, and an appropriate growth medium was added. Forty-eight hours later, the supernatant was removed, filtered through a 0.45 um filter, and then aliquoted and stored at −70° C. Here, it is necessary to select the envelope DNA which can infect well depending on the characteristics of cell into which retrovirus is transferred. Among the three known envelope DNA types, RD114 envelope DNA having the best transfer efficiency to primary T cells was used to produce retroviruses.

Example 4: Peripheral Blood Mononuclear Cell Isolation and Culture 4-1. Primary Peripheral Blood Mononuclear Cell (PBMC) Isolation Human blood was collected and centrifuged to isolate peripheral blood mononuclear cell (PBMC).

First, an equal amount of 1×PBS+2% FBS solution was added to the collected blood. Then, 3 mL of Ficoll-Paque PLUS (GE healthcare) was placed under the barrier through the central hole of SepMate™-50 (STEMCELL technologies), and the premixed blood mixture was slowly raised at a rate of 10 mL to avoid mixing on the Ficoll, and centrifuged at 1200×g for 10 minutes. Centrifuged tubes have gradient formed, so the uppermost layer of plasma is first removed and then the cloudy peripheral blood mononuclear cell (PBMC) layer is transferred to a new tube using a pipette. Here, red blood cells may come out along with it, so care should be taken not to take too large layer. The PBMC which was transferred into a new tube, was mixed with 5 ml of 1×PBS+2% FBS solution, centrifuged at 300×g for 8 minutes, all supernatant except for pellet was removed, and allowed to repeat the procedure once more. Finally obtained PBMC pellet is resuspended in primary T cell growth medium and grown in a 37° C. 5% CO₂ incubator.

4-2. Primary T Cell Culture

PBMC isolated as above is prepared at 1×10⁶ cells/ml, cultured in a 100 mm dish, and then added 50 ng/ml of anti-CD3 (eBioscience). Here, AIMV media (gibco) to which 5% heat-inactivated human serum was added was used as T cell growth medium, and 300 U/ml of human interleukin-2 (hIL-2) was mixed at every medium replacement. Subsequently, subculture of the primary T cell was carried out once every four days in the T75 flask while maintaining a constant concentration (0.7×10⁵ to 2×10⁶ cells/ml).

Example 5: Retroviral Transfection to Primary T Cells

Each retrovirus was transferred into primary T cells at a rate of 4.8×10¹⁰ copies/each transfer once a day for 2 times in total. Specifically, before transfer of retrovirus into the cells, the bottom of the culture dish was coated with retronectin at 20 μg/well for 2 hours at room temperature. After 2 hours, retronectin was removed, blocking reagent (PBS w/2.5% human albumin) was added at 2 ml/well, followed by incubation at room temperature for 30 minutes. Then, the retrovirus frozen at −70° C. was rapidly thawed and mixed with the T cell culture medium at a ratio of 1:1, placed in the retronectin-coated dish, and then allowed for the retrovirus to adhere for 2 hours at 2000 g, 32° C. In the meantime, the primary T cells were prepared by counting the number of cells at 5×10⁵ cells/ml. After leaving only about 1 ml of medium in the centrifuged culture dish, the prepared cells were added at 4 ml/well and centrifuged at 1000 g for 15 minutes. The centrifuged culture dish was carefully taken and cultured in a 37° C. 5% CO₂ incubator for one day. This procedure was repeated once the next day.

Example 6: Measurement of CTLA-4 Expression Amount by Semi-Quantitative PCR in Retrovirus-Transfected Primary T Cells After reverse-transcription of the RNA obtained from the primary T cells into which ribozyme-expressing retrovirus was transferred, semi-quantitative PCR was performed to confirm the intracellular level of CTLA-4. Experiments were run in triplet for each sample, averaged, and the melting point was examined and confirmed on agarose gel. Here, measurement was made using SYBR Green, and a quantified standard control was used to compare samples in semi-quantitative manner. For calibration, RT-efficiency difference between samples was corrected using the values calculated from 18S semi-quantitative PCR performed with the same RT sample as used in CTLA-4 PCR. Here, as a primer, 5' primer (CTLA-4 real F) and 3' primer (CTLA-4 real R) were used.

Figure 5:
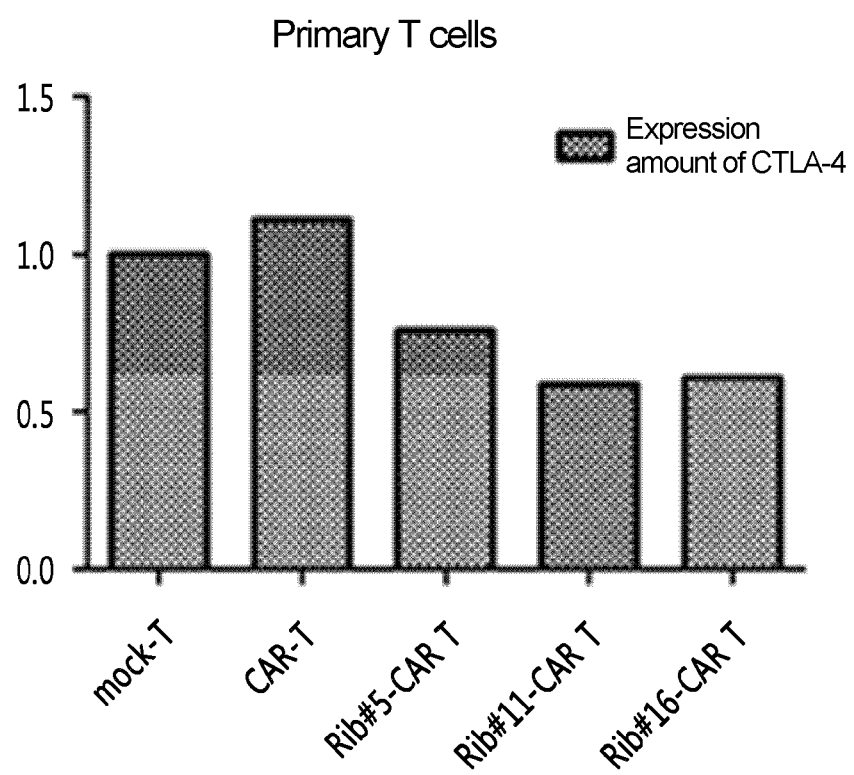
FIG. 5 shows the results of an experiment in which clones (Rib #5, Rib #11 and Rib #16) were obtained by constructing a retroviral vector with IGS48 ribozyme, RNA was obtained from primary T cells into which these clones were transferred, and was reverse-transcripted, and then semi-quantitative PCR was performed to confirm the intracellular level of CTLA-4.

The clones obtained in Example 3 were compared with each other in order to obtain clones best expressed in consideration of clonal variation. Specifically, the retroviruses expressing ribozyme were transferred into primary T cells, respectively, and CTLA-4 RNA levels in T cells were confirmed. Here, T cell (CAR T) into which CAR-expressing retrovirus was transferred was used together with, as a control, T cell (mock-T) into which virus was not transferred. As a result, the reduction of CTLA-4 RNA could be confirmed in T cells (rib #5/11/16-CAR T, respectively) into which ribozyme-expressing retrovirus was transferred, and among three clones, #11 and #16 were confirmed to be more efficient (FIG. 5).

Example 7: Measurement Through Western Blotting

The primary T cells into which retrovirus was transferred were washed with 1×PBS, and then treated with 50 μl of 1×RIPA buffer (Sigma) and 0.1M PMSF (Fluka) mixture, scraped with scrapers, and then all transferred to a 1.5 ml tube. Cell debris was removed by centrifugation and only the supernatant was collected in a new tube to obtain total whole extract. The obtained total protein was quantified by Bradford assay (Sigma), wherein BSA was used as a standard for quantification.

20 μg of the quantified protein and 4× sample buffer (Invitrogen) were mixed at 3:1, followed by protein denaturation at 95° C. for 5 minutes, and then prepared in a state of being incubated on ice. SDS-PAGE gels (NuPAGE 4-12% Bis-Tris minigel, Invitrogen) were prepared and immersed in running buffer (1× NuPAGE MES SDS Running buffer, Invitrogen), and protein samples were slowly loaded onto each lane of the gel. Then, the gel was run at 200V for 35 minutes and the resulting gel was transferred onto a PVDF membrane at 12V for 60 minutes.

After the transfer was completed, the membrane was carefully removed, washed once with TBS, and then treated at room temperature for 30 minutes, while shaking, with a blocking solution which was prepared by adding 5% skim milk in 1×TBST (1×TBS+0.5% tween20). All blocking solution was then removed and the membrane was treated overnight at 4° C., while shaking, with a new blocking solution which was diluted at 1:500 with the mouse anti-human CD247 (BD) as a primary antibody. After completion of the primary antibody treatment, all solution was removed, and the membrane was treated at room temperature for 1 hour with a new blocking solution which was diluted at 1:5000 with goat anti-mouse IgG HRP (Thermo) as a secondary antibody. After completion of all antibody treatments, the membrane was washed three times for 15 minutes each with 1×TBST, and then the detection reagent (Santacruz) including luminol was mixed at a ratio of A:B=1:1, spread throughout the membrane, and then allowed to react for 1 minute under dark condition, and bands were confirmed on Gel-doc (ImageQuant LAS4000, GE healthcare).

Figure 6:
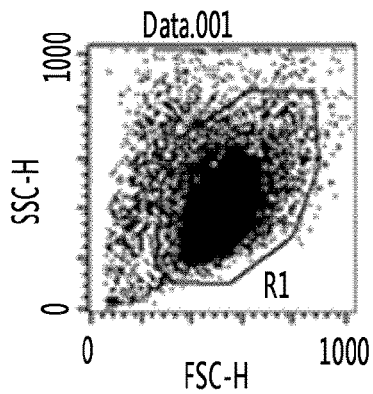
FIG. 6 shows the results of an experiment in which clones (Rib #5, Rib #11 and Rib #16) were obtained by constructing a retroviral vector with IGS48 ribozyme, and each cell was measured through FACS to confirm the expression level of CAR on the surface of the T cell into which these clones were transferred.
Figure 6:
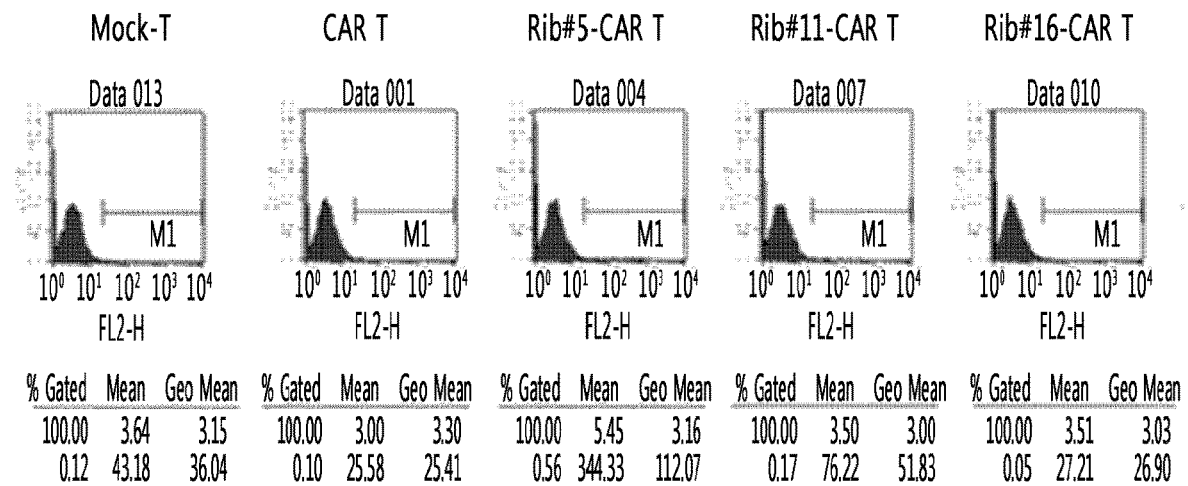
Figure 6:
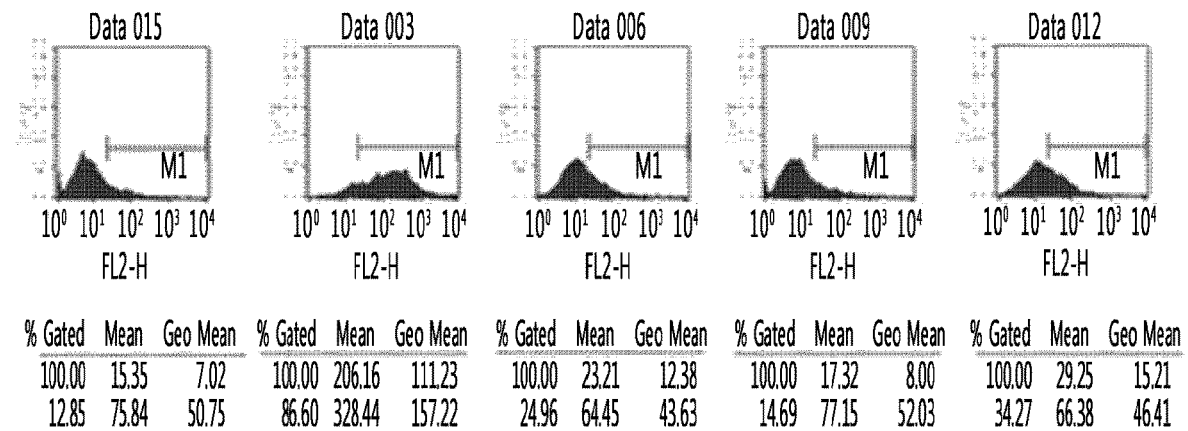

The clones obtained in Example 3 were compared with each other in order to obtain clones best expressed in consideration of clonal variation. Specifically, CAR expression was confirmed and compared by Western blotting and FACS. As a result, CAR expression could be confirmed in ribozyme-expressing T cells (Rib #5/11/16-CAR T, respectively). First, FACS data could confirm that CAR was expressed in all of T cells into which ribozyme-expressing retrovirus was transferred, and the highest expression was observed in #16 clone (FIG. 6).

Also, it was confirmed through Western blotting that CAR was expressed in Rib #5/16-CAR T. However, in Rib #5/16-CAR, it was confirmed that the expression amount of CAR was lower than that of CAR T without CTLA-4-targeting ribozyme. On the other hand, it was confirmed that the expression amount of CAR in Rib #11-CAR T was insufficient (FIG. 7).

Summary of the above results could confirm reduction of target RNA and expression of CAR in T cells into which CTLA-4-targeting ribozyme-expres sing retrovirus was transferred, and the highest efficiency was observed in clone 16.

Example 8: Confirmation of Apoptosis-Inducing Effects on Cancer Cells Expressing Tag72

A ribozyme was cloned into the retroviral vector, and then transferred into primary T cells, and confirmed whether the T cells exhibited cell-killing ability on the cell line LS174T expressing the Tag72 antigen. Cell-killing experiments were carried out by transferring, into primary T cells, the retroviral vector, which was constructed as virus (Ret-CTLA-4 Rib48-CAR, Rib #16-CAR T) by cloning ribozyme-CAR into a retroviral vector.

Specifically, LS174T cell line was prepared as a target cell at $1\times10^4$ cells/50 µl, and 0.2 µl of CellTox green dye (Promega) was added per 50 µl of the prepared cells and mixed. Then, the mixture was aliquoted to a black 96-well plate at 50 µl/well. Then, the T cell (Effector cell) into which retrovirus was transferred, was resuspended in the culture medium according to the ratio (target cell:effector cell+1:5, 1:10, 1:20, 1:30), and then mixed with the target cell at 50 µl/well. LS174T or effector cell alone was added as a background control for the cytotoxicity assay and an equal amount of growth media was added to exclude the influence of the medium. Here, since the CellTox green dye (Promaga) was not contained in the well containing effector cell only, the target growth medium mixed, at a ratio as above, with the dye was added. In addition, an equal amount of effector cell growth media was added to the wells containing LS174T only as a toxicity control (positive control), and 4 µl of lysis solution was added. As a negative control, an equal amount of dye was added to the wells containing only a mixture of two cell culture media. The plate was filled as described above, and a light-blocked environment was created. The reaction was allowed to perform in a 37° C. $CO_2$ incubator for 24 hours, and then measured on a fluorescence reader (Ex 485 nm/Em 520 nm).

Example 9: Jurkat Cell Line Stimulation and Retrovirus Transfer

Jurkat cell line was aliquoted to $1\times10^6$ cells/well/2 ml (RPMI 1640), and after 24 hours, retrovirus was mixed with RPMI 1640 medium to give a total volume of 3 ml at $3\times10^9$ copies/well, and allowed to replace medium in each well. Here, polybrene (8 µg/ml) was also added at 1µ/ml. Cell down was then performed at 32° C., 2800 rpm for 90 minutes to transfer retrovirus, and incubated for 2 hours in a $CO_2$ incubator. At medium replacement after 2 hours, 2 ml of RPMI1640 mixed with PMA (50 ng/ml)+PHA (1 ug/ml) was added. After incubation for 72 hours in a $CO_2$ incubator, cells were harvested to obtain RNA.

TABLE 1

| \multicolumn{2}{c}{Primers used} ||
| Primer | Sequence (5' → 3') |
|---|---|
| RY-RT (SEQ ID NO: 18) | ATGTGCTGCAAGGCGATT |
| RY-TS (SEQ ID NO: 19) | TGTAAAACGACGGCCAGTG |
| CTLA4 5' UTR XhoI (SEQ ID NO: 20) | CCGCTCGAGCTTCTGTGTG TGCACATG |
| IGS48P1P10 StuI (SEQ ID NO: 21) | GAAGGCCTATCCTATGGAT AGAAAAGTTATCAGGCAT |
| IGS111P1P10 StuI (SEQ ID NO: 22) | GAAGGCCTATCCTTTGCCT TTAAAAGTTATCAGGCAT |
| IGS232P1P10 StuI (SEQ ID NO: 23) | GAAGGCCTATCCTTTGACA GGAAAAGTTATCAGGCAT |
| 5' F.luci ScaI P10 IGS48 (SEQ ID NO: 24) | AAAAGTACTCGTTAGGATG CCCACCATGGAAGACGCCA AAAACATA |
| 5' F.luci ScaI P10 IGS111 (SEQ ID NO: 25) | AAAAGTACTCGTAAGGATG CCCACCATGGAAGACGCCA AAAACATA |
| 5' F.luci ScaI P10 IGS232 (SEQ ID NO: 26) | AAAAGTACTGTAAGGATGC CCACCACGAAGACGCCAAA AACATA |
| IGS48 P1P10 HindIII (SEQ ID NO: 27) | CCCAAGCTTATCCTATGGA TAGAAAAGTTATCAGGCAT |

TABLE 1-continued

Primers used

| Primer | Sequence (5' → 3') |
|---|---|
| IGS111 P1P10 HindIII (SEQ ID NO: 28) | CCCAAGCTTATCCTTTGCC TTTAAAAGTTATCAGGCAT |
| IGS232 P1P10 HindIII (SEQ ID NO: 29) | CCCAAGCTTATCCTTTGAC AGGAAAAGTTATCAGGCAT |
| 3' F.luci end XhoI (SEQ ID NO: 30) | CCGCTCGAGTTACAATTTG GACTTTCCGCCCTT |
| IGS48 AS100 kit F (SEQ ID NO: 31) | CGTTTAAACTTAAGCTTAG CCATGGCTTTATGGGA |
| IGS48 AS300 kit F (SEQ ID NO: 32) | CGTTTAAACTTAAGCTTAC CTCAGTGGCTTTGCCT |
| IGS48 AS kit R (SEQ ID NO: 33) | ATGGATCCGCGAAGCTTTG ATTCTGTGTGGGTTCA |
| IGS48 BamHI F (SEQ ID NO: 34) | CGCGGATCCATCCTATGGA TAGAAAAG |
| IGS48Rib BamHI R (SEQ ID NO: 35) | CGCGGATCCATCCTAACGA GTACTCCA |
| CTLA4 real F (SEQ ID NO: 36) | CTACCTGGGCATAGGCAAC G |
| CTLA4 real R (SEQ ID NO: 37) | CCCCGAACTAACTGCTGCA A |

Experiments using, as positive control, T cell (CAR T) into which CAR-expressing retrovirus with no ribozyme (Ret-CAR) was transferred showed about 5-fold cytotoxicity compared to mock T cell, which corresponded to about 70% of the positive control group (FIG. 8).

Example 10: Construction of Promoter-Added Ribozyme

On the other hand, in Examples 1 to 4, the present inventors constructed ribozyme into which an antisense sequence was introduced, and confirmed from its trans-splicing effects that the efficiency was not improved (FIG. 4). Thus, in order to enhance the effect of ribozyme, to the basic CTLA4 Rib48-CAR ribozyme (SEQ ID NO: 8) was added 100 nt of antisense to obtain ribozyme constructs (SEQ ID NO: 9 and SEQ ID NO: 11), and added a CMV promoter to obtain ribozyme constructs (SEQ ID NO: 10 and SEQ ID NO: 11). These constructs were cloned into retroviral vectors and the retroviral vectors were transferred into primary T cells to compare and confirm their respective cell-killing effects.

Example 11: Development of Constructs with CMV Promoter and Antisense Ligated to Increase Specificity and Target Efficiency of Ribozyme and Confirmation of Expression of CAR and Decreased Expression of CTLA-4

Retroviral vectors were constructed with IGS48 ribozyme, which was confirmed to exhibit the highest activity through the above Examples, and the next experiment was conducted with Rib #16 (hereinafter referred to as Rib), which is most efficient among them.

Figure 9:
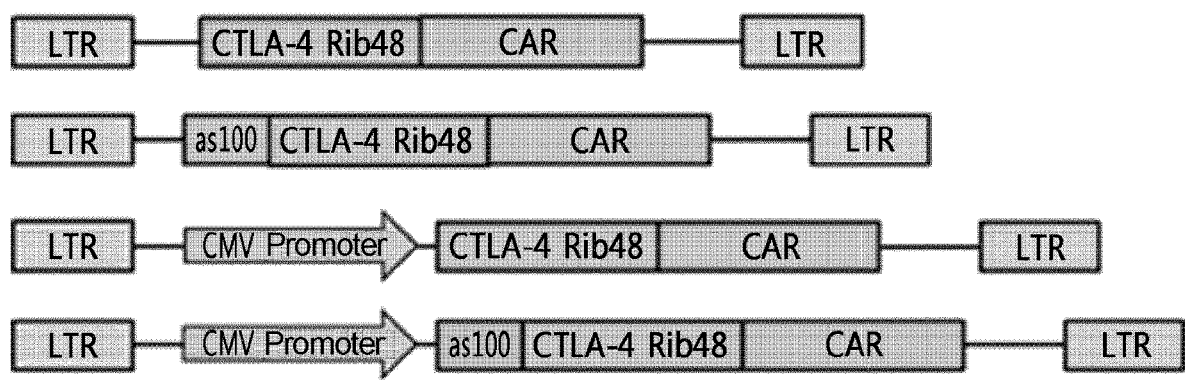
FIG. 9 is a schematic diagram showing the constitution of expression cassettes of CTLA4 Rib48-CAR, AS100-CTLA4 Rib48-CAR, CMV-CTLA4 Rib48-CAR, and CMV-AS-CTLA4 Rib48-CAR, which are typically used in the present invention. That is, each construct was constructed depending on whether an antisense sequence was introduced or a CMV promoter was introduced.

In order to increase CTLA-4-targeting specificity and efficiency of a ribozyme, a CMV promoter or 100 nt of antisense to CTLA-4 was ligated before the retroviral promoter, and then experiments were conducted to compare their efficiency. Specifically, the following constructs were constructed: Ret-CTLA-5 Rib48-CAR(Rib-CAR T) construct having the structure of [CTLA-4 Rib48-CAR], Ret-AS-CTLA-5 Rib48-CAR(AS-Rib-CAR T) construct having the structure of [antisense 100 nt-CTLA-4 Rib48-CAR], Ret-CMV-CTLA-5 Rib48-CAR(CMV-Rib-CAR T) construct having the structure of [CMV promoter-CTLA-4 Rib48-CAR], and Ret-CMV-AS-CTLA-5 Rib48-CAR (CMV-AS-Rib-CAR T) construct having the structure of [CMV promoter-antisense 100 nt-CTLA-4 Rib48-CAR]; wherein, a construct having only a CMV promoter placed in retroviral vector was constructed and used as a positive control in which a CMV promoter was ligated (FIG. 9).

To confirm CAR expression in each T cell, PBMC were transfected with each retroviral vector and FACS was performed to confirm the extracellular expression of CAR.

As a result, as can be seen from FIG. 10, high expression of CAR was observed in Rib-CAR T in which only ribozyme is present, and low expression of CAR was observed in T cells transfected with other constructs. Low expression of CAR was also observed in CMV-CAR T in which only a CMV promoter is placed.

The level of CTLA-4 RNA in the T cell into which the retrovirus used in the above experiment was transferred, was also confirmed. Among the T cells to which ribozyme was delivered, the amount of CTLA-4 RNA was measured in Rib-CAR T, which showed the highest expression of CAR, and CMV-AS-Rib-CAR T, which was the second highest expression of CAR, wherein as a control, T cell (CAR T) into which CAR-expressing retrovirus was transferred was used together with T cell (mock T) into which no virus was transferred were used.

Figure 11:
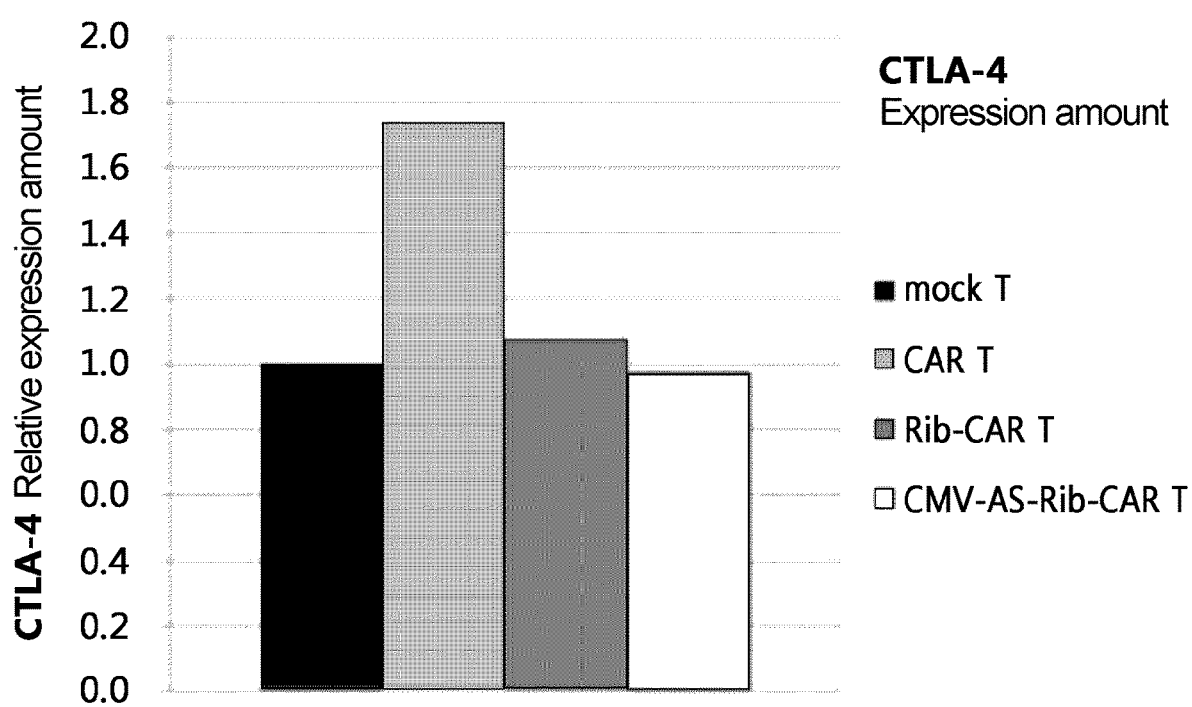
FIG. 11 is a diagram in which the level of CTLA-4 RNA was confirmed by transferring Rib-CAR T and CMV-AS-Rib-CAR T, among the ribozymes of the present invention, via a retrovirus into T cells.

As a result, as can be seen from FIG. 11, compared to mock T, the level of CTLA-4 RNA was observed to be about 2-fold as high in CAR T, which is a control into which retrovirus was transferred. This could confirm that the expression of CTLA-4 is increased when retrovirus is transferred. Therefore, it was thought that the expression of CTLA-4 was also increased in other T cells into which ribozyme-expressing retrovirus was transferred.

As a result, the CTLA-4 RNA level of Rib-CAR T and CMV-AS-Rib-CAR T was observed to be similar to mock T, and this might be interpreted as the increased amount of CTLA-4 by retrovirus being decreased by ribozyme, thereby making its level similar to that of mock T.

Example 12: Effect of Retrovirus Transfer on Intracellular CTLA-4 RNA Level

In order to confirm the increased expression of CTLA-4 in retrovirus-infected cells as described above, experiments were carried out in Jurkat cell line (human T lymphocyte; acute T cell leukemia). Here, for retroviruses used, Ret-CAR expressing CAR only was used as a positive control for CAR and the CTLA-4 RNA level was compared using PMA/PHA chemical known to activate Jurkat cell and thus enhance CTLA-4 expression.

Figure 12:
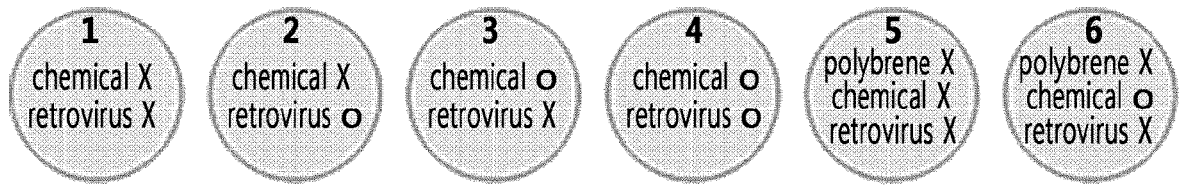
FIG. 12 is a diagram which summarizes the results of confirming the level of CTLA-4 RNA by treating Jurkat cells with a chemical, that increases the level of CTLA-4 RNA in Jurkat cells, and/or a retrovirus, that delivers ribozyme of the present invention. First, the experimental condition of each experimental group is summarized in the upper section. Specifically, experimental group II-1 was not treated with any of chemical or retrovirus; experimental group II-2 was not treated with chemical and was treated with retrovirus; experimental group II-3 was treated with chemical and was not treated with retrovirus; experimental group II-4 was treated with both chemical and retrovirus; experimental group II-5 was not treated with any of polybrene, chemical or retrovirus; and experimental group II-6 was not treated with polybrene and retrovirus, and was treated with chemical. In the lower section, there is shown a diagram in which CTLA-4 RNA level of the above experimental groups was measured.
Figure 12:
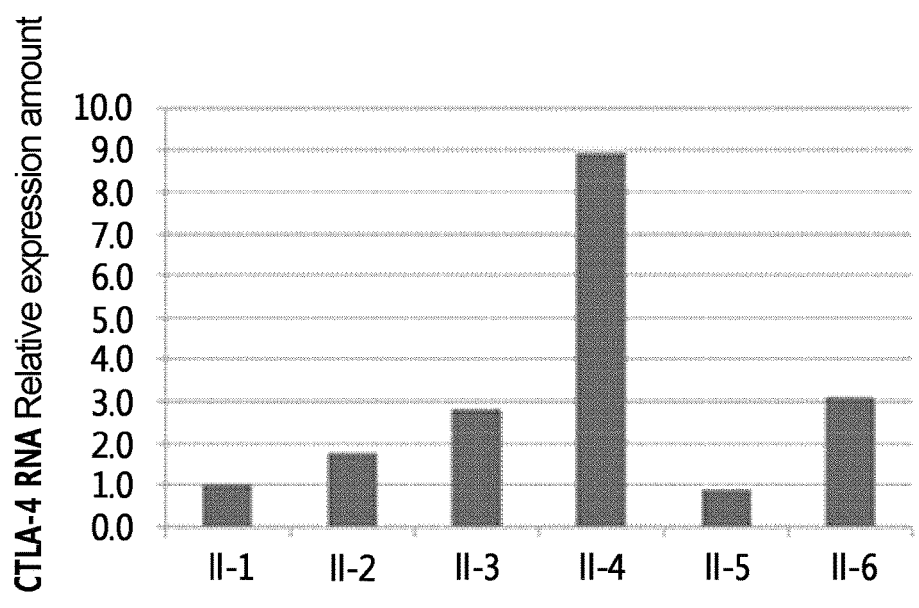

As a result, as can be seen from FIG. 12, it was confirmed that the CTLA-4 RNA level was increased about 2-fold as high when only retrovirus was transferred into the cells (II-2) just as in the previous experiments; increased about 3-fold as high when only chemical was treated; and increased on the order of about 9-fold as high in the control simultaneously treated with retrovirus and chemical.

In other words, the above results show that the expression amount of CTLA-4 was increased even when only retrovirus was transferred, as the level of CTLA-4 was increased through chemical in Jurkat cells; and this, in turn, confirmed that ribozyme decreased the increased level of CTLA-4 RNA, compared to mock T, after retrovirus was transferred as in Example 10.

Example 13: Cytotoxicity Assay for Target Cancer Cells

A ribozyme was cloned into a retroviral vector, then the retroviral vector was transferred into primary T cells and confirmed as to whether it shows cytotoxic effects on LS174T cell line expressing the Tag72 antigen.

Confirmation was made for the target-killing ability of Rib-CAR and CMV-AS-Rib-CAR, which are the ones identified in the above Examples to show decreased CTLA-4 RNA level and highest expression of CAR.

As a result, as can be seen from FIG. 13, the Rib-CAR T showed a killing ability of about 50% of CAR T, which is a positive control, and Rib-CAR was confirmed to have better killing ability than that of CMV-AS-Rib-CAR. Therefore, consistent with the results of previous experiments, it was finally confirmed that Rib-CAR showed the highest CTLA-4 RNA-targeting efficiency and the excellent CAR-expressing efficiency, which makes it a construct having the best cancer cell-targeting/killing ability.

From the foregoing, a person skilled in the art to which the present invention pertains will be able to understand that the present invention may be embodied in other specific forms without modifying the technical ideas or essential characteristics of the present invention. In this regard, the embodiments described herein are only for illustrative purposes and should not be construed as limiting the scope of the present invention. The present invention is intended to cover not only the exemplary embodiments but also various alternatives, modifications, equivalents and other embodiments that may be included within the spirit and scope of the present invention as defined by the appended claims

The invention claimed is:

1. A recombinant vector, comprising a cytotoxic T-lymphocyte-associated protein-4 (CTLA-4)-targeting trans-splicing ribozyme expression cassette for delivery of a chimeric antigen receptor, wherein the expression cassette includes: (i) a CTLA-4-targeting trans-splicing ribozyme; and (ii) a polynucleotide encoding a chimeric antigen receptor connected to 3' exon of the ribozyme.

2. The recombinant vector of claim 1, wherein the CTLA-4-targeting trans-splicing ribozyme includes a nucleic acid sequence selected from the group consisting of SEQ ID NO: 1, SEQ ID NO: 2, SEQ ID NO: 3, and SEQ ID NO: 38.

3. The recombinant vector of claim 1, wherein the chimeric antigen receptor recognizes a cancer cell-specific antigen.

4. The recombinant vector of claim 3, wherein the cancer cell-specific antigen is selected from the group consisting of Epithelial glycoprotein 2 (EGP2), Epithelial glycoprotein 40 (EGP40), Tumor associated glycoprotein 72 (TAG72), Interleukin 13 receptor alpha-2 subunit (IL13Rα2), Carbonic anhydrase IX (CA IX), CD19, CD52, CD33, CD20, TSLPR, CD22, CD30, GD3, CD171, Anaplastic lymphoma kinase (ALK), CD47, EGFRvIII, Neural cell adhesion molecule (NCAM), Folate binding protein (FBP), Lewis-Y antigen (Le(Y)), Mucin 1 (MUC1), Prostate stem cell antigen (PSCA), Prostate-specific membrane antigen (PSMA), Fibroblast growth factor receptor 4 (FGFR4), Fetal acetylcholine receptor (FAR), Carcinoembryonic antigen (CEA), Human epidermal growth factor receptor 2 (HER2), Mesothelin, Hyaluronate receptor variant 6 (CD44v6), B7-H3, Glypican-3,5, ROR1, Survivin, folate receptor (FOLR1), Wilm's tumor antigen (WT1), CD70, and Vascular endothelial growth factor 2 (VEGFR2).

5. The recombinant vector of claim 3, wherein polynucleotide encoding the chimeric antigen receptor included in the recombinant vector includes a nucleic acid sequence of SEQ ID NO: 4.

6. The recombinant vector of claim 1, further comprising, at 5' end of the ribozyme, (iii) a polynucleotide of an antisense sequence to 50 to 400 nucleotides of a base sequence downstream of a ribozyme's recognition site on the CTLA-4.

7. The recombinant vector of claim 6, wherein the antisense sequence includes a nucleic acid sequence of SEQ ID NO: 5 or 6.

8. A ribozyme expressed from the recombinant vector of claim 1.

9. A retrovirus expressing the ribozyme according to claim 8.

10. A T cell treated with the retrovirus according to claim 9.

11. A pharmaceutical composition for preventing or treating cancers, the pharmaceutical composition comprising, as an effective ingredient, the recombinant vector of of claim 1 and/or the T cell of claim 10.

12. The pharmaceutical composition for preventing or treating cancers of claim 11, wherein the cancer is selected from the group consisting of lung cancer, pancreatic cancer, liver cancer, melanoma, bone cancer, breast cancer, colon cancer, leukemia, uterine cancer, ovarian cancer, lymphoma, and brain cancer.

13. A method for treating cancers, the method comprising administering, to an individual in need thereof, a pharmaceutically effective amount of the recombinant vector of claim 1 and/or the T cell of claim 10.

* * * * *